(12) United States Patent
Gobeil et al.

(10) Patent No.: US 11,213,597 B2
(45) Date of Patent: Jan. 4, 2022

(54) KININ-BASED THERANOSTIC PROBES FOR SOLID CANCERS AND USES THEREOF

(71) Applicant: SOCIETE DE COMMERCIALISATION DES PRODUITS DE LA RECHERCHE APPLIQUEE SOCPRA SCIENCES SANTE ET, Sherbrooke (CA)

(72) Inventors: Fernand Gobeil, Sherbrooke (CA); Brigitte Guerin, Sherbrooke (CA); Martin Lepage, Compton (CA); Robert Sabbagh, Sherbrooke (CA); David Fortin, Sherbrooke (CA)

(73) Assignee: SOCIETE DE COMMERCIALISATION DES PRODUITS DE LA RECHERCHE APPLIQUEE SOCPRA SCIENCES SANTE ET HUMAINES S.E.C., Sherbrooke (CA)

( * ) Notice: Subject to any disclaimer, the term of this patent is extended or adjusted under 35 U.S.C. 154(b) by 0 days.

(21) Appl. No.: 15/738,671

(22) PCT Filed: Jun. 23, 2016

(86) PCT No.: PCT/CA2016/050732
§ 371 (c)(1),
(2) Date: Dec. 21, 2017

(87) PCT Pub. No.: WO2016/205914
PCT Pub. Date: Dec. 29, 2016

(65) Prior Publication Data
US 2018/0311385 A1 Nov. 1, 2018

Related U.S. Application Data

(60) Provisional application No. 62/184,268, filed on Jun. 25, 2015.

(51) Int. Cl.
| | | |
|---|---|---|
| A61K 51/08 | (2006.01) | |
| C07K 7/06 | (2006.01) | |
| C07K 7/18 | (2006.01) | |
| A61K 38/04 | (2006.01) | |
| C07K 1/13 | (2006.01) | |
| G01N 33/574 | (2006.01) | |
| C07K 14/72 | (2006.01) | |

(52) U.S. Cl.
CPC ............. A61K 51/088 (2013.01); C07K 7/06 (2013.01); C07K 7/18 (2013.01); C07K 14/723 (2013.01); G01N 33/57434 (2013.01); *A61K 38/043* (2013.01); *A61K 2123/00* (2013.01); *C07K 1/13* (2013.01); *G01N 33/57415* (2013.01); *G01N 33/57423* (2013.01)

(58) Field of Classification Search
CPC ........ A61K 38/00; A61K 49/00; A61K 51/00; A61K 51/08; A61K 51/088; A61K 2121/00; A61K 2123/00; A61K 38/043; C07K 1/13; C07K 14/723; C07K 7/06; C07K 7/18; G01N 33/57434; G01N 33/57415; G01N 33/57423
USPC .......... 424/1.11, 1.65, 1.69, 1.81, 1.85, 1.89, 424/9.1, 9.2, 9.3, 9.4, 9.5, 9.6; 534/7, 534/10–16; 514/1, 1.1; 530/300
See application file for complete search history.

(56) References Cited

U.S. PATENT DOCUMENTS

| | | | | |
|---|---|---|---|---|
| 7,211,566 | B2* | 5/2007 | Regoli | C07K 7/18 514/12.2 |
| 7,932,228 | B2* | 4/2011 | Nantel | A61K 31/282 514/12.5 |
| 8,076,453 | B2* | 12/2011 | Gobeil, Jr | C07K 7/18 530/328 |
| 10,039,846 | B2* | 8/2018 | Lin | C07D 241/04 |
| 2015/0238641 | A1* | 8/2015 | Lin | C07D 241/50 424/1.69 |

FOREIGN PATENT DOCUMENTS

| | | | | |
|---|---|---|---|---|
| WO | | 201440192 | 3/2014 | |
| WO | WO-2014040192 | A1 * | 3/2014 | ........... A61K 51/088 |

OTHER PUBLICATIONS

Flook et al. "Substitution of the Lys Lonker woth the β-Ala Linker Dramatically Decreased the Renal Uptake of 99mTc-Labelled Arg-X-Asp-Conjugated and X-Ala-Asp-Conjugated a-Melanpcyte Stimulating Hormone Peptides", Journal of Medicinal Chemistry, 2014, 57, 9010-9018.
K.-S. Lin et al. "Comparative Studies of Three 68Ga-Labeled [Des-Arg10]Kallidin Derivatives for Imaging Bradykinin B1 Receptor Expression with PET", The Jounral of Nuclear Medecine, vol. 56, No. 4, Apr. 1, 2018, pp. 622-627.
Jessie R. Nedrow et al. "Position Emission Tomographic Imaging of Cooper 64—and Gallium 68-Labeled Chelator Conjugates of the Somatostatin Agonist Tyr3—Octreotate", Molecular Imaging, vol. 13, No. 7, Sep. 1, 2014.
Srinivasarao et al., Nature Rev Drug Discov, 2015, 14: 203-219.
Limperis et al., Bioconjugate Chem, 2018, 29: 1774-1784.

* cited by examiner

*Primary Examiner* — D. L. Jones
(74) *Attorney, Agent, or Firm* — Norton Rose Fulbright Canada LLP

(57) ABSTRACT

It is provided new chemical entities allowing simultaneous diagnosis and treatment of cancers. More specifically, it is provided a theranostic compound consisting of a stabilized peptide ligand (agonists and antagonists) for the kinin B1 receptors (B1R) conjugated to specific radionuclides (e.g. $^{64}Cu$) suitable for dual imaging/radiotherapy applications.

2 Claims, 5 Drawing Sheets

Specification includes a Sequence Listing.

A)

B)

KININ-BASED THERANOSTIC PROBES FOR SOLID CANCERS AND USES THEREOF

CROSS-REFERENCE TO RELATED APPLICATIONS

This application is a U.S. National Phase of International Application No. PCT/CA2016/050732, filed on Jun. 23, 2016 and claiming priority from U.S. provisional patent application 62/184,268 filed Jun. 25, 2015, and this application claims priority to and the benefit of the above-identified applications, each of which are incorporated by reference herewith in their entirety.

TECHNICAL FIELD

The present disclosure relates to a theranostic compound consisting of a stabilized peptide ligand (agonists and antagonists) for the kinin B1 receptors (B1R) conjugated to specific radioisotopes (e.g. $^{64}$Cu) suitable for dual imaging/radiotherapy applications for cancers.

BACKGROUND ART

Mortality due to primary and secondary (metastatic) brain cancer has essentially remained unchanged since four decades. Moreover, the incidence of metastatic brain tumors is rising in the wake of improved therapy for systemic cancers e.g. lung, breast, and skin cancers. Primary and secondary brain cancers are both fatal, if left untreated. Gliomas account for 78% of all malignant primary brain tumors and are the top cause of brain cancer-related death Computed tomography (CT) and magnetic resonance imaging (MRI) remain sub-adequate tools for the purposes of brain cancer diagnosis. [$^{18}$F]FDG is inadequate for PET brain-tumor imaging due to the high metabolic demands of normal brain cells which consume large amounts of glucose, resulting in high background signal. [$^{18}$F]FDG is also of limited use for detection of low-grade glioma and residual/recurrent glioma.

Therapeutic approaches to malignant glioma, as well as brain metastases, include surgery, radiotherapy and chemotherapy. Far from being effective, these approaches remain for the most part palliative. The highly infiltrative nature of malignant glioma and particularly GBM—the highest grade glioma—precludes complete surgical removal. Remaining tumor cells inevitably renew tumor masses. Radiotherapy cannot eradicate scattered hypoxic microscopic tumor foci, undetectable by standard imaging e.g. FDG-PET and MRI. Whole-brain irradiation often induces neurological deterioration. Chemotherapy for brain cancer most often has a low therapeutic index, important systemic side effects and do not readily cross the blood-tumor barrier in sufficient amount to be effective. A fundamental change in diagnostic and therapeutic strategies is urgently needed.

There is still a need to be provided with new therapeutic approaches to malignant glioma, as well as brain metastases.

SUMMARY

In accordance with the present description there is now provided a theranostic compound comprising a peptide binding specifically to B1R, and a "dual-purpose" radionuclide suitable for both imaging and therapy of cancer.

In an embodiment, the theranostic compound comprises
a) a radioactive element, that allows both the detection and the radiation therapy of brain cancer; and
b) a targeting element that recognizes the kinin B1 receptor (B1R) expression such as in brain cancer cells and associated blood vessels upon its systemic administration, and which may also promote reversible opening of the blood-brain barrier (BBB) allowing adequate brain entry of the theranostic compound.

In an embodiment, the radioactive element is a radionuclide.

In another embodiment, the radionuclide is at least one the $^{64/67}$Cu, $^{131}$I, $^{111}$In $^{153}$Sm, $^{89}$Sr, $^{90}$Y, $^{177}$Lu and $^{213}$Bi.

In an embodiment, the theranostic compound further comprises a chelating agent binding to the bioactive element, limiting the probability of in vivo transmetallation of the bioactive element, and a linker between said radionuclide and said peptide binding specifically to B1R.

In another embodiment, the targeting element is an agonist or an antagonist of the B1R.

In a supplemental embodiment, the targeting element is DLys$^1$-Arg$^2$-Pro$^3$-Hyp$^4$-Gly$^5$-Igl$^6$-Ser$^7$-Pro$^8$-DPhe$^9$-OH (SEQ ID NO: 3), Orn$^1$-Arg$^2$-Pro$^3$-Hyp$^4$-Gly$^5$-Igl$^6$-Ser$^7$-Pro$^8$-DPhe$^9$-OH (SEQ ID NO: 4) or Orn$^1$-Arg$^2$-Oic$^3$-Pro$^4$-Gly$^5$-(αMe)Phe$^6$-Ser$^7$-DβNal$^8$-Ile$^9$-OH (SEQ ID NO: 5).

In an embodiment, the cyclic chelating agent is NOTA or its derivatives; methylhydroxamates derived from triaza- and tetraazamacrocycles (NOTHA$_2$ and DOTHA$_2$); 1,4,7-triazacyclononane-1-glutaric acid-4,7-diacetic acid (NODAGA) or its derivatives; diethylenetriaminepentaacetate (DTPA) or its derivatives; 1,4,7,10-tetraazadodecanetetraacetate (DOTA) and its derivatives; 1,4,7,10-tetraazadodecane-1,4,7-triacetate (D03A) and its derivatives; 3,6,9,15-tetraazabicyclo[9.3. 1]pentadeca-1 (15),11,13-triene-3,6,9-triacetic acid) (PCTA) or its derivatives; 1,4,7,10-tetraazacyclotridecanetetraacetic acid (TRITA) and its derivatives; 1,4,8,11-tetraazacyclotetradecane-1,4,8,1 1-tetraacetic acid (TETA) and its derivatives; 1,4,7,10-tetraazadodecanetetramethylacetate (DOTMA) and its derivatives; 1,4,7,10-tetraazadodecane-1,4,7-trimethylacetate (D03MA) and its derivatives; N,N',N'',N'''-tetraphosphonatomethyl-1,4,7,10-tetraazacyclododecane (DOTP) and its derivatives; 1,4,7, 10-tetraazacyclododecane-1,4,7, 10-tetrakis(methylene methylphosphonic acid) (DOTMP) and its derivatives; 1,4,7,10-tetraazacyclododecane-1,4,7,10-tetrakis(methylene phenylphosphonic acid) (DOTPP) and its derivatives; or N,N'-ethylenedi-L-cysteine or its derivatives.

In an embodiment, the linker is a β-alanine residue, 2-aminoethyl-piperazine-1-carboxylic acid (APCA-dicationic) or amino-hexanedioic-1-acid (AHDA-dianionic) or derivatives.

In another embodiment, the theranostic compound is $^{64}$Cu-NOTA-βAla-Orn$^1$-Arg$^2$-Oic$^3$-Pro$^4$-Gly$^5$-(αMe)Phe$^6$-Ser$^7$-DβNal$^8$-Ile$^9$-OH (SEQ ID NO: 6).

In another embodiment, the theranostic compound is $^{64}$Cu-NOTA-βAla-DLys$^1$-Arg$^2$-Pro$^3$-Hyp$^4$-Gly$^5$-Igl$^6$-Ser$^7$-Pro$^8$-DPhe$^9$-OH (SEQ ID NO: 7).

In another embodiment, the theranostic compound is $^{64}$Cu-NOTA-βAla-Orn$^1$-Arg$^2$-Pro$^3$-Hyp$^4$-Gly$^5$-Igl$^6$-Ser$^7$-Pro$^8$-DPhe$^9$-OH (SEQ ID NO: 8).

In another embodiment, the theranostic compound is at least one of:
$^{64}$Cu-NOTA-βAla-Orn$^1$-Arg$^2$-Oic$^3$-Pro$^4$-Gly$^5$-(αMe)Phe$^6$-Ser$^7$-DβNal$^8$-Ile$^9$-OH (SEQ ID NO: 6);
$^{64}$Cu-NOTA-βAla-Orn$^1$-Arg$^2$-Oic$^3$-Pro$^4$-Gly$^5$-Cha$^6$-Ser$^7$-DβNal$^8$-Ile$^9$-OH (SEQ ID NO: 9);
$^{64}$Cu-NOTA-βAla-Orn$^1$-Arg$^2$-Oic$^3$-Pro$^4$-Gly$^5$-Igl$^6$-Ser$^7$-DβNal$^8$-Ile$^9$-OH (SEQ ID NO: 10);
$^{64}$Cu-NOTA-βAla-Orn$^1$-Arg$^2$-Oic$^3$-Pro$^4$-Gly$^5$-Thi$^6$-Ser$^7$-DβNal$^8$-Ile$^9$-OH (SEQ ID NO: 11);

$^{64}$Cu-NOTA-βAla-Orn$^1$-Arg$^2$-Oic$^3$-Pro$^4$-Gly$^5$-(L or D)Cpg$^6$-Ser$^7$-DβNal$^8$-Ile$^9$-OH (SEQ ID NO: 12);
$^{64}$Cu-NOTA-βAla-(L or D)Lys$^1$-Arg$^2$-Oic$^3$-Pro$^4$-Gly$^5$-(αMe)Phe$^6$-Ser$^7$-DβNal$^8$-Ile$^9$-OH (SEQ ID NO: 13);
$^{64}$Cu-NOTA-βAla-(L or D)Lys$^1$-Arg$^2$-Oic$^3$-Pro$^4$-Gly$^5$-Cha$^6$-Ser$^7$-DβNal$^8$-Ile$^9$-OH (SEQ ID NO: 14);
$^{64}$Cu-NOTA-βAla-(L or D)Lys$^1$-Arg$^2$-Oic$^3$-Pro$^4$-Gly$^5$-Igl$^6$-Ser$^7$-DβNal$^8$-Ile$^9$-OH (SEQ ID NO: 15);
$^{64}$Cu-NOTA-βAla-(L or D)Lys$^1$-Arg$^2$-Oic$^3$-Pro$^4$-Gly$^5$-Thi$^6$-Ser$^7$-DβNal$^8$-Ile$^9$-OH (SEQ ID NO: 16);
$^{64}$Cu-NOTA-βAla-(L or D)Lys$^1$-Arg$^2$-Oic$^3$-Pro$^4$-Gly$^5$-(L or D)Cpg$^6$-Ser$^7$-DβNal$^6$-Ile$^9$-OH (SEQ ID NO: 17);
$^{64}$Cu-NOTA-βAla-(L or D)Arg$^1$-Arg$^2$-Oic$^3$-Pro$^4$-Gly$^5$-(αMe)Phe$^6$-Ser$^7$-DβNal$^8$-Ile$^9$-OH (SEQ ID NO: 18);
$^{64}$Cu-NOTA-βAla-(L or D)Arg$^1$-Arg$^2$-Oic$^3$-Pro$^4$-Gly$^5$-Cha$^6$-Ser$^7$-DβNal$^8$-Ile$^9$-OH (SEQ ID NO: 19);
$^{64}$Cu-NOTA-βAla-(L or D)Arg$^1$-Arg$^2$-Oic$^3$-Pro$^4$-Gly$^5$-Igl$^6$-Ser$^7$-DβNal$^8$-Ile$^9$-OH (SEQ ID NO: 20);
$^{64}$Cu-NOTA-βAla-(L or D)Arg$^1$-Arg$^2$-Oic$^3$-Pro$^4$-Gly$^5$-Thi$^6$-Ser$^7$-DβNal$^8$-Ile$^9$-OH (SEQ ID NO: 21);
$^{64}$Cu-NOTA-βAla-(L or D)Arg$^1$-Arg$^2$-Oic$^3$-Pro$^4$-Gly$^5$-(L or D)Cpg$^6$-Ser$^7$-DβNal$^8$-Ile$^9$-OH (SEQ ID NO: 22);
$^{64}$Cu-NOTHA$_2$-βAla-Orn$^1$-Arg$^2$-Oic$^3$-Pro$^4$-Gly$^5$-(αMe)Phe$^6$-Ser$^7$-DβNal$^8$-Ile$^9$-OH (SEQ ID NO: 6);
$^{64}$Cu-NOTHA$_2$-βAla-Orn$^1$-Arg$^2$-Oic$^3$-Pro$^4$-Gly$^5$-Cha$^6$-Ser$^7$-DβNal$^8$-Ile$^9$-OH (SEQ ID NO: 9);
$^{64}$Cu-NOTHA$_2$-βAla-Orn$^1$-Arg$^2$-Oic$^3$-Pro$^4$-Gly$^5$-Igl$^6$-Ser$^7$-DβNal$^8$-Ile$^9$-OH (SEQ ID NO: 10);
$^{64}$Cu-NOTHA$_2$-βAla-Orn$^1$-Arg$^2$-Oic$^3$-Pro$^4$-Gly$^5$-Thi$^e$-Ser$^7$-D3Nal$^8$-Ile$^9$-OH (SEQ ID NO: 11);
$^{64}$Cu-NOTHA$_2$-βAla-Orn$^1$-Arg$^2$-Pro$^3$-Pro$^4$-Gly$^5$-(L or D)Cpg$^6$-Ser$^7$-Pro$^8$-DPhe$^9$-OH (SEQ ID NO: 23);
$^{64}$Cu-NOTHA$_2$-βAla-(L or D)Lys$^1$-Arg$^2$-Oic$^3$-Pro$^4$-Gly$^5$-(αMe)Phe$^6$-Ser$^7$-DβNal$^8$-Ile$^9$-OH (SEQ ID NO: 13);
$^{64}$Cu-NOTHA$_2$-βAla-(L or D)Lys$^1$-Arg$^2$-Oic$^3$-Pro$^4$-Gly$^5$-Cha$^6$-Ser$^7$-DβNal$^8$-Ile$^9$-OH (SEQ ID NO: 14);
$^{64}$Cu-NOTHA$_2$-βAla-(L or D)Lys$^1$-Arg$^2$-Oic$^3$-Pro$^4$-Gly$^5$-Igl$^6$-Ser$^7$-DβNal$^8$-Ile$^9$-OH (SEQ ID NO: 15);
$^{64}$Cu-NOTHA$_2$-βAla-(L or D)Lys$^1$-Arg$^2$-Oic$^3$-Pro$^4$-Gly$^5$-Thi$^6$-Ser$^7$-DβNal$^8$-Ile$^9$-OH (SEQ ID NO: 16);
$^{64}$Cu-NOTHA$_2$-βAla-(L or D)Lys$^1$-Arg$^2$-Oic$^3$-Pro$^4$-Gly$^5$-(L or D)Cpg$^6$-Ser$^7$-DβNal$^8$-Ile$^9$-OH (SEQ ID NO: 17);
$^{64}$Cu-NOTHA$_2$-βAla-(L or D)Arg$^1$-Arg$^2$-Oic$^3$-Pro$^4$-Gly$^5$-(αMe)Phe$^6$-Ser$^7$-DβNal$^8$-Ile$^9$-OH (SEQ ID NO: 18);
$^{64}$Cu-NOTHA$_2$-βAla-(L or D)Arg$^1$-Arg$^2$-Oic$^3$-Pro$^4$-Gly$^5$-Cha$^6$-Ser$^7$-DβNal$^8$-Ile$^9$-OH (SEQ ID NO: 19);
$^{64}$Cu-NOTHA$_2$-βAla-(L or D)Arg$^1$-Arg$^2$-Oic$^3$-Pro$^4$-Gly$^5$-Igl$^6$-Ser$^7$-DβNal$^8$-Ile$^9$-OH (SEQ ID NO: 20);
$^{64}$Cu-NOTHA$_2$-βAla-(L or D)Arg$^1$-Arg$^2$-Oic$^3$-Pro$^4$-Gly$^5$-Thi$^6$-Ser$^7$-DβNal$^8$-Ile$^9$-OH (SEQ ID NO: 21);
$^{64}$Cu-NOTHA$_2$-βAla-(L or D)Arg$^1$-Arg$^2$-Oic$^3$-Pro$^4$-Gly$^5$-(L or D)Cpg$^6$-Ser$^7$-DβNal$^8$-Ile$^9$-OH (SEQ ID NO: 22);
$^{64}$Cu-NOTA-βAla-Orn$^1$-Arg$^2$-Pro$^3$-Pro$^4$-Gly$^5$-(αMe)Phe$^6$-Ser$^7$-Pro$^8$-DPhe$^9$-OH (SEQ ID NO: 24);
$^{64}$Cu-NOTA-βAla-Orn$^1$-Arg$^2$-Pro$^3$-Pro$^4$-Gly$^5$-(L or D)Phe$^6$-Ser$^7$-Pro$^8$-DPhe$^9$-OH (SEQ ID NO: 25);
$^{64}$Cu-NOTA-βAla-Orn$^1$-Arg$^2$-Pro$^3$-Pro$^4$-Gly$^5$-(L or D)Cha$^6$-Ser$^7$-Pro$^8$-DPhe$^9$-OH (SEQ ID NO: 26);
$^{64}$Cu-NOTA-βAla-Orn$^1$-Arg$^2$-Pro$^3$-Pro$^4$-Gly$^5$-(L or D)Igl$^6$-Ser$^7$-Pro$^8$-DPhe$^9$-OH (SEQ ID NO: 27);
$^{64}$Cu-NOTA-βAla-Orn$^1$-Arg$^2$-Pro$^3$-Pro$^4$-Gly$^5$-(L or D)Cpg$^6$-Ser$^7$-Pro$^8$-DPhe$^9$-OH (SEQ ID NO: 23);
$^{64}$Cu-NOTA-βAla-(L or D)Lys$^1$-Arg$^2$-Pro$^3$-Pro$^4$-Gly$^5$-(αMe)Phe$^6$-Ser$^7$-Pro$^8$-DPhe$^9$-OH (SEQ ID NO: 28);
$^{64}$Cu-NOTA-βAla-(L or D)Lys$^1$-Arg$^2$-Pro$^3$-Pro$^4$-Gly$^5$-(L or D)Phe$^5$-Ser$^7$-Pro$^8$-DPhe$^9$-OH (SEQ ID NO: 29);

$^{64}$Cu-NOTA-13Ala-(L or D)Lys$^1$-Arg$^2$-Pro$^3$-Pro$^4$-Gly$^5$-(L or D)Cha$^6$-Ser$^7$-Pro$^8$-DPhe$^9$-OH (SEQ ID NO: 30);
$^{64}$Cu-NOTA-βAla-(L or D)Lys$^1$-Arg$^2$-Pro$^3$-Pro$^4$-Gly$^5$-(L or D)Igl$^6$-Ser$^7$-Pro$^8$-DPhe$^9$-OH (SEQ ID NO: 31);
$^{64}$Cu-NOTA-βAla-(L or D)Lys$^1$-Arg$^2$-Pro$^3$-Pro$^4$-Gly$^5$-(L or D)Cpg$^6$-Ser$^7$-Pro$^8$-DPhe$^9$-OH (SEQ ID NO: 32);
$^{64}$Cu-NOTA-βAla-(L or D)Arg$^1$-Arg$^2$-Pro$^3$-Pro$^4$-Gly$^5$-(L or D)Phe$^6$-Ser$^7$-Pro$^8$-DPhe$^9$-OH (SEQ ID NO: 33);
$^{64}$Cu-NOTA-βAla-(L or D)Arg$^1$-Arg$^2$-Pro$^3$-Pro$^4$-Gly$^5$-(L or D)Cha$^6$-Ser$^7$-Pro$^8$-DPhe$^9$-OH (SEQ ID NO: 34);
$^{64}$Cu-NOTA-βAla-(L or D)Arg$^1$-Arg$^2$-Pro$^3$-Pro$^4$-Gly$^5$-(L or D)Igl$^6$-Ser$^7$-Pro$^8$-DPhe$^9$-OH (SEQ ID NO: 35);
$^{64}$Cu-NOTA-βAla-(L or D)Arg$^1$-Arg$^2$-Pro$^3$-Pro$^4$-Gly$^5$-(L or D)Cpg$^6$-Ser$^7$-Pro$^8$-DPhe$^9$-OH (SEQ ID NO: 36);
$^{64}$Cu-NOTA-βAla-Lys$^1$-Arg$^2$-Pro$^3$-Pro$^4$-Gly$^5$-Phe$^6$-Ser$^7$-Pro$^8$-DPhe$^9$-OH (SEQ ID NO: 39);
$^{64}$Cu-NOTA-βAla-Arg$^1$-Arg$^2$-Pro$^3$-Pro$^4$-Gly$^5$-Phe$^6$-Ser$^7$-Pro$^8$-DPhe$^9$-OH (SEQ ID NO: 40);
$^{64}$Cu-NOTA-βAla-(N(ε)-methyl)Lys$^1$-Arg$^2$-Pro$^3$-Pro$^4$-Gly$^5$-Phe$^6$-Se$r^7$-Pro$^8$-DPhe$^9$-OH (SEQ ID NO: 41);
$^{64}$Cu-NOTA-βAla-(N(α)-methyl)Lys$^1$-Arg$^2$-Pro$^3$-Pro$^4$-Gly$^5$-Phe$^6$-Ser$^7$-Pro$^8$-DPhe$^9$-OH (SEQ ID NO: 42);
$^{64}$Cu-NOTA-βAla-Lys$^1$ψ(CH$_2$—NH)-Arg$^2$-Pro$^3$-Pro$^4$-Gly$^5$-Phe$^6$-Ser$^7$-Pro$^8$-DPhe$^9$-OH (SEQ ID NO: 43);
$^{64}$Cu-NOTHA$_2$-βAla-Orn$^1$-Arg$^2$-Pro$^3$-Pro$^4$-Gly$^5$-(αMe)Phe$^6$-Ser$^7$-Pro$^8$-DPhe$^9$-OH (SEQ ID NO: 24);
$^{64}$Cu-NOTHA$_2$-βAla-Orn$^1$-Arg$^2$-Pro$^3$-Pro$^4$-Gly$^5$-(L or D)Phe$^6$-Ser$^7$-Pro$^8$-DPhe$^9$-OH (SEQ ID NO: 25);
$^{64}$Cu-NOTHA$_2$-βAla-Orn$^1$-Arg$^2$-Pro$^3$-Pro$^4$-Gly$^5$-(L or D)Cha$^6$-Ser$^7$-Pro$^8$-DPhe$^9$-OH (SEQ ID NO: 26);
$^{64}$Cu-NOTHA$_2$-βAla-Orn$^1$-Arg$^2$-Pro$^3$-Pro$^4$-Gly$^5$-(L or D)Igl$^6$-Ser$^7$-Pro$^8$-DPhe$^9$-OH (SEQ ID NO: 27);
$^{64}$Cu-NOTHA$_2$-βAla-Orn$^1$-Arg$^2$-Pro$^3$-Pro$^4$-Gly$^5$-(L or D)Cpg$^6$-Ser$^7$-Pro$^8$-DPhe$^9$-OH (SEQ ID NO: 37);
$^{64}$Cu-NOTHA$_2$-βAla-(L or D)Lys$^1$-Arg$^2$-Pro$^3$-Pro$^4$-Gly$^5$-(αMe)Phe$^6$-Ser$^7$-Pro$^8$-DPhe$^9$-OH (SEQ ID NO: 28);
$^{64}$Cu-NOTHA$_2$-βAla-(L or D)Lys$^1$-Arg$^2$-Pro$^3$-Pro$^4$-Gly$^5$-(L or D)Phe$^6$-Ser$^7$-Pro$^8$-DPhe$^9$-OH (SEQ ID NO: 29);
$^{64}$Cu-NOTHA$_2$-βAla-(L or D)Lys$^1$-Arg$^2$-Pro$^3$-Pro$^4$-Gly$^5$-(L or D)Cha$^6$-Ser$^7$-Pro$^8$-DPhe$^9$-OH (SEQ ID NO: 30);
$^{64}$Cu-NOTHA$_2$-βAla-(L or D)Lys$^1$-Arg$^2$-Pro$^3$-Pro$^4$-Gly$^5$-(L or D)Igl$^6$-Ser$^7$-Pro$^8$-DPhe$^9$-OH (SEQ ID NO: 31);
$^{64}$Cu-NOTHA$_2$-βAla-(L or D)Lys$^1$-Arg$^2$-Pro$^3$-Pro$^4$-Gly$^5$-(L or D)Cpg$^6$-Ser$^7$-Pro$^8$-DPhe$^9$-OH (SEQ ID NO: 32;
$^{64}$Cu-NOTHA$_2$-βAla-(L or D)Arg$^1$-Arg$^2$-Pro$^3$-Pro$^4$-Gly$^5$-(L or D)Phe$^6$-Ser$^7$-Pro$^8$-DPhe$^9$-OH (SEQ ID NO: 33);
$^{64}$Cu-NOTHA$_2$-βAla-(L or D)Arg$^1$-Arg$^2$-Pro$^3$-Pro$^4$-Gly$^5$-(L or D)Cha$^6$-Ser$^7$-Pro$^8$-DPhe$^9$-OH (SEQ ID NO: 34);
$^{64}$Cu-NOTHA$_2$-βAla-(L or D)Arg$^1$-Arg$^2$-Pro$^3$-Pro$^4$-Gly$^5$-(L or D)Igl$^6$-Ser$^7$-Pro$^8$-DPhe$^9$-OH (SEQ ID NO: 35); and
$^{64}$Cu-NOTHA$_2$-Ala-(L or D)Arg$^1$-Arg$^2$-Pro$^3$-Pro$^4$-Gly$^5$-(L or D)Cpg$^6$-Ser$^7$-Pro$^8$-DPhe$^9$-OH (SEQ ID NO: 36).

In another embodiment, the compound is in free base form or in salt form.

In an embodiment, the theranostic compound described herein is for detecting and/or treating brain cancer, breast cancer, lung cancer or prostate cancer.

In another embodiment, the brain cancer is a primary or secondary brain cancer.

In a further embodiment, the theranostic compound described herein is for targeted radionuclide therapy of brain cancer, breast cancer, lung cancer or prostate cancer.

In a further embodiment, the theranostic compound described herein is formulated for delivery by at least one route consisting of intravenous, intraarterial, subcutaneous, intramuscular, intracranial, intraventricular, intraspinal, intrathecal and intranasal.

It is also provided the use of the theranostic compound as described herein for the imaging of the residual tumor mass postoperatively in a subject.

It is also provided the use of the theranostic compound as described herein for the non-invasive evaluation of the efficacy of novel oncotherapies in a subject.

It is also provided the use of the theranostic compound as described herein to compare the size of a tumor tissue detected before and after a cancer treatment in a subject.

In an embodiment, the subject is an animal or a human.

It is also provided the use of the theranostic compound as described herein in the manufacture of a medicament for targeted radionuclide therapy of brain cancer, breast cancer, lung or prostate cancer.

It is also provided the use of the theranostic as described herein for imaging a tissue in a subject.

It is also provided the use of the theranostic as described herein for evaluating the efficacy of a cancer treatment to prevent or reduce the size of tumors in a subject.

It is also provided the use of the theranostic as described herein for the imaging of the residual tumor mass postoperatively.

In an embodiment, the method described herein further comprises the step of comparing the size of the tissue detected before and after cancer treatment.

It is also provided the use of the theranostic as described in the manufacture of a medicament for treating brain cancer, breast cancer, lung cancer and prostate cancer.

It is also provided a method of detecting cancer cells.

In an embodiment, the cancer cell is a brain cancer cell or a tumor.

In an embodiment, the cancer cell or tumor is from a prostate cancer, lung cancer or a breast cancer.

In an embodiment, the subject is ongoing cancer treatment.

As used herein, abbreviations of natural α-amino acids are those accepted in the art. The prefix small capital letter D- or L-denotes the amino acid stereochemistry. Other abbreviations are described as follows: Thi, α-(2-thienyl)-L-alanine; Orn, L-ornithine; β-Nal, β-(2-naphthyl)-alanine; Igl, 2-indanyl-glycine; Cha, cyclohexyl-alanine; Cpg, α-cyclopentyl-alanine; Oic, 2-Carboxyoctahydroindole and (αMe)Phe, α-methyl-phenylalanine; APCA, 2-aminoethyl-piperazine-1-carboxylic acid; AHDA, amino-hexanedioic-1-acid; Hyp is 4-hydroxyproline.

BRIEF DESCRIPTION OF THE DRAWINGS

Reference will now be made to the accompanying drawings.

FIGS. 4A-C illustrate in vitro cell uptake and anticancer activity of $^{64}$Cu-NOTA-βAla-Orn$^1$-Arg$^2$-Oic$^3$-Pro$^4$-Gly$^5$-(αMe)Phe$^6$-Ser$^7$-DβNal$^8$-Ile$^9$-OH; $^{64}$Cu-NOTA-B1RA) (SEQ ID NO: 6) in human prostate cancer cells (PC3 and LN-CaP). Cell uptake of $^{64}$Cu-Nota-B1RA (in the presence or not of competitor R954) in PC3 cells measured at 20 h post-treatment by radiometric assays (A). Dose-dependent antiproliferative effects of $^{64}$Cu-acetate and $^{64}$Cu/Nota-B1RA on PC3 cells (B) and LN-CaP cells (C), assessed by clonogenic assays. FIG. 4 D illustrates the molecular imaging of prostate cancer with $^{64}$Cu/Nota-B1RA. PET images of LN-CaP tumor-bearing nude mouse obtained after injection of 64Cu/Nota-B1RA (9 MBq) at 0.5 h post-injection (p.i.). FIG. 4E shows the tumor-to-muscle uptake ratio for $^{64}$Cu/Nota-B1RA with or without co-injection of the competitor R954 in the LN-CaP tumor model. FIG. 4F confirms the immunohistochemical (IHC) overexpression of B1R in tumoral tissues of LNCaP-bearing mice (blackiste dark-color).

DETAILED DESCRIPTION

Figure 1:
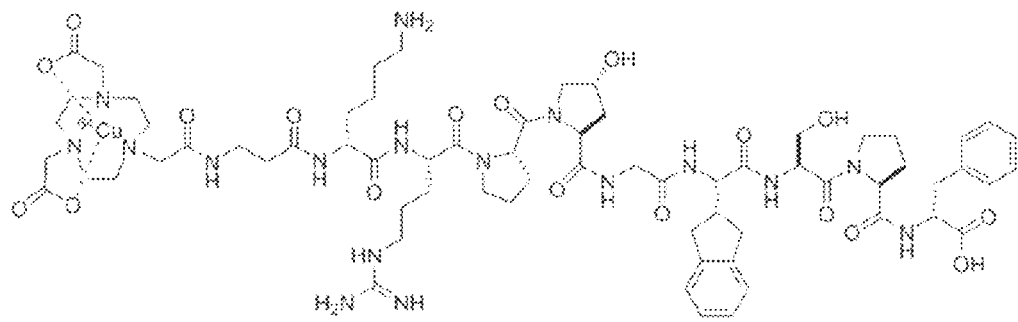
FIG. 1 illustrates the structures of one embodiment, consisting of the theranostic compounds A)$^{64}$Cu-NOTA-βAla-DLys$^1$-Arg$^2$-Pro$^3$-Hyp$^4$-Gly$^5$-Igl$^6$-Ser$^7$-Pro$^8$-DPhe$^9$-OH (SEQ ID NO: 7) and B)$^{64}$Cu-NOTA-βAla-Orn$^1$-Arg$^2$-Oic$^3$-Pro$^4$-Gly$^5$-(αMe)Phe$^6$-Ser$^7$-DβNal$^8$-Ile$^9$-OH (SEQ ID NO: 6).
Figure 1:
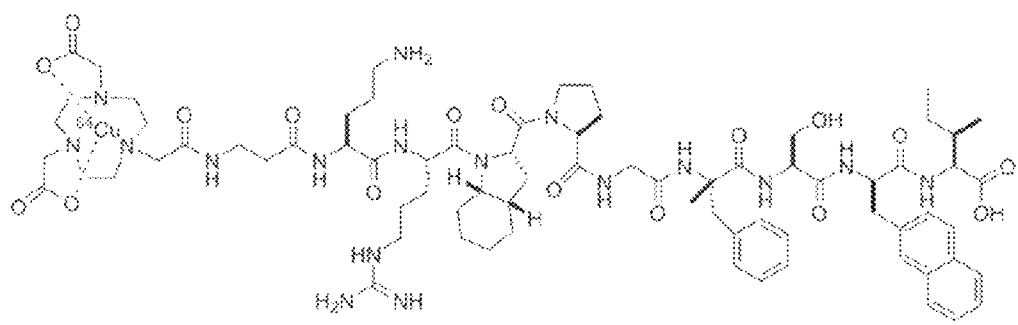

It is provided herein new chemical entities allowing simultaneous diagnosis and treatment of brain cancer. More specifically, the disclosure relates to peptide ligands (agonists and antagonists) for the kinin B1 receptors conjugated to specific radioisotopes (e.g. $^{64}$Cu) tailored with desirable features for dual imaging/radiotherapy applications, such as high affinity and stability, efficient clearance and effective cancer cell/nuclear uptake.

It is thus provided a specific nuclear probe targeting B1R for theranostic of brain cancer including brain metastases i.e. cancers, such as breast, lung, and skin cancers, which have spread to the brain.

Kinins are short linear peptides that exert multiple effects throughout the body. The effects of kinins are mediated through specific activation of two types of receptors, namely, the kinin B1 (B1R) and B2 receptors (B2R), both belonging to the G-protein coupled receptor (GPCR) family. Contrary to most GPCRs, B1R is inducible, resistant to internalization and less prone to desensitization upon ligand activation. B1R is induced or overexpressed under inflammatory conditions, including tissue injury, sepsis, cardiovascular diseases and cancers. Overexpression of B1R in brain cancer specimens was reported.

The GPCR kinin B1 receptors (B1R) are a highly promising target for cancer diagnosis and treatment because B1R is inducible and plays no role in normal physiology thus limiting its potential side effects (Figueroa et al., 2012, Expert Opin Ther Targets, 16: 299-312; Whalley et al., 2012, Expert Opin Drug Discov, 7:1129-1148). Moreover, B1R is part of the molecular signature of all forms of solid cancers tested to date (Figueroa et al., supra), including brain cancer (Côté et al., 2012, PLoS One., 7:e37485), and B1R antagonist peptides inhibit cancerous growth in preclinical models of cancer (Whalley et al., supra).

U.S. Pat. No. 7,211,566, the content of which is incorporated herein by reference, describes a high affinity, biostable, antagonist peptide targeting B1R of various mammalian species; namely the AcOrn$^1$-Arg$^2$-Oic$^3$-Pro$^4$-Gly$^5$-(αMe)Phe$^6$-Ser$^7$-DβNal$^8$-Ile$^9$-OH (R-954; SEQ ID NO: 1).

U.S. Pat. No. 7,932,228, the content of which is incorporated herein by reference, describes the anticancer activity of R-954 in bone and prostate cancers.

U.S. Pat. No. 8,076,453, the content of which is incorporated herein by reference, describes novel kinin B1R peptide agonists having strong affinities and selectivity for the B1R, increased in vivo resistance to enzymatic degradation, superior pharmacokinetic properties to those of naturally occurring compounds, capacity to significantly enhance delivery of substances across the BBB and within peripheral tissues for the treatment of tumors. Examples of such B1R agonist peptides include the Sar$^0$-Lys$^1$-Arg$^2$-Pro$^3$-Hyp$^4$-Gly$^5$-Phe$^6$-Ser$^7$-Pro$^8$-DPhe$^9$-OH (SEQ ID NO: 2) (U.S. Pat. No. 8,076,453).

WO 2014040192 describes compositions targeting B1R for medical imaging of cancer and other disorders. Recombinant B1R overexpressed in non-malignantly transformed HEK-293 kidney cells were chosen in the proof-of-concept studies. PET data based solely on heterologous expression systems (e.g. HEK-293 cells) harboring high-level of GPCRs may be problematic as tumor-specific uptake is highly dependent on protein receptor level (Fani et al., supra). This may actually lead to overestimation of radiotracer selectivity/specificity and provide misleading or unrepresentative evidence of expected utility in clinical practice. The B1R radiolabeled peptides that have been tested so far for PET imaging showed imperfect in vitro/in vivo stabilities against off-target peptidases that are present in blood and tissues (Liu et al., 2015, Mol Pharm, 12(3): 974-982; Lin et al., 2015, Cancer Res, 75: 387-393; Lin et al., 2015, J Nucl Med, 56(4): 622-627), and this may possibly represent causes of false-positive results. The occurrence of potentially toxic radiotracer metabolites, especially in high-dose radiation therapy, is also of concern. Thus, despite the peptide tracers of the prior art, it is provided herein first-in-class non-hydrolysable, high-affinity theranostics agents with no off-target interactions in order to improve imaging of different types of cancer, including and treatment of brain cancer.

Copper-64 ($^{64}$Cu) is a suitable radionuclide for cancer theranostic applications. $^{64}$Cu (β$^+$, 0.65 MeV [17.8%] for PET imaging; β$^-$, 0.58 MeV [38.4%] along with Auger electrons [40%] for radiotherapy) has decay characteristics that allow its use for PET imaging and targeted radiotherapy of cancer. $^{64}$Cu has a mean positron energy similar to that of $^{18}$F and a half-life of 12.7 h, ideal for PET imaging and radiotherapy. $^{64}$Cu emits a β$^-$ particle with a short penetration range in tissue (2.5 mm) more suitable for relatively small tumor masses. Data shows that delivery of $^{64}$Cu to the cell nuclei actually enhance its therapeutic effect. Indeed, $^{64}$Cu also emits a 6.84-key Auger electron (40%) with a penetration range of about 5 μm, which may be highly toxic when DNA is within range; most of this energy is delivered within a sphere of several nanometers around the decay site.

The development of effective brain theranostics lies on the successful completion of several requirements which are difficult to predict experimentally. These requirements were reviewed recently include the following: 1) radioligand diffusivity across the blood-brain barrier, 2) specific recognition of the radioligand to the tumor cell surface, 3) internalization and recycling of the receptor, and 4) nuclear uptake of radionuclides whether they are linked or not to the peptide ligands.

It is disclosed herein specific theranostics targeting B1R by the addition of a radiometal chelating group on the N-terminus of the peptide ligand scaffold extended by a linker residue. Such chemical modifications are well tolerated, as exemplified by compounds Cu-NOTA-βAla-Orn$^1$-Arg$^2$-Oic$^3$-Pro$^4$-Gly$^5$-(αMe)Phe$^6$-Ser$^7$-DβNal$^8$-Ile$^9$-OH (SEQ ID NO: 6) (IC$_{50}$ values: B1R: 5 nM; hB2R: >10 μM) and Cu/NOTHA$_2$-βAla-Lys$^1$-Arg$^2$-Pro$^3$-Pro$^4$-Gly$^5$-Phe$^6$-Ser$^7$-Pro$^8$-DPhe$^9$-OH (EC$_{50}$ values: B1R: 33 μM; hB2R: >10 μM), which show remarkable high affinities/selectivities for their cognate B1R, comparable to their unmodified parent peptides, as assessed in human B1R (hB1R) bioassays (Côté el al., 2009, Peptides, 30: 788-795). Furthermore, the nature/type of the linker unit (e.g. βAla, APCA (dicationic) and AHDA (dioanionic))) plays an essential role in maintaining apparent affinities of the theranostic compositions as its absence can result in a drastic drop in affinity to hB1R (ex. 10-fold decrease in the case of Cu-NOTA-Orn$^1$-Arg$^2$-Oic$^3$-Pro$^4$-Gly$^5$-(αMe)Phe$^6$-Ser$^7$-DβNal$^8$-Ile$^9$-OH (SEQ ID ON: 5) (IC$_{50}$ value: 50 nM)). The chemical nature of the linker unit may also influence the pharmacokinetics of theranostics.

Figure 2:
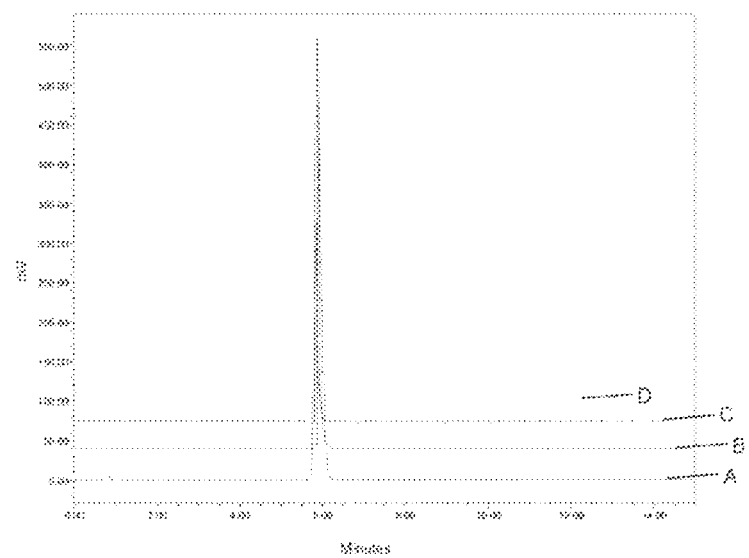
FIG. 2 shows representative UPLC radiometric profiles of in vitro stability studies of the $^{64}$Cu-NOTA-βAla-Orn$^1$-Arg$^2$-Oic$^3$-Pro$^4$-Gly$^5$-(αMe)Phe$^6$-Ser$^7$-DβNal$^8$-Ile$^9$-OH (SEQ ID NO: 6) (A), following copper formulation (B), or treated with 100% rat plasma at 37° C. for 2 h (C) and 20 h (D).
Figure 3:
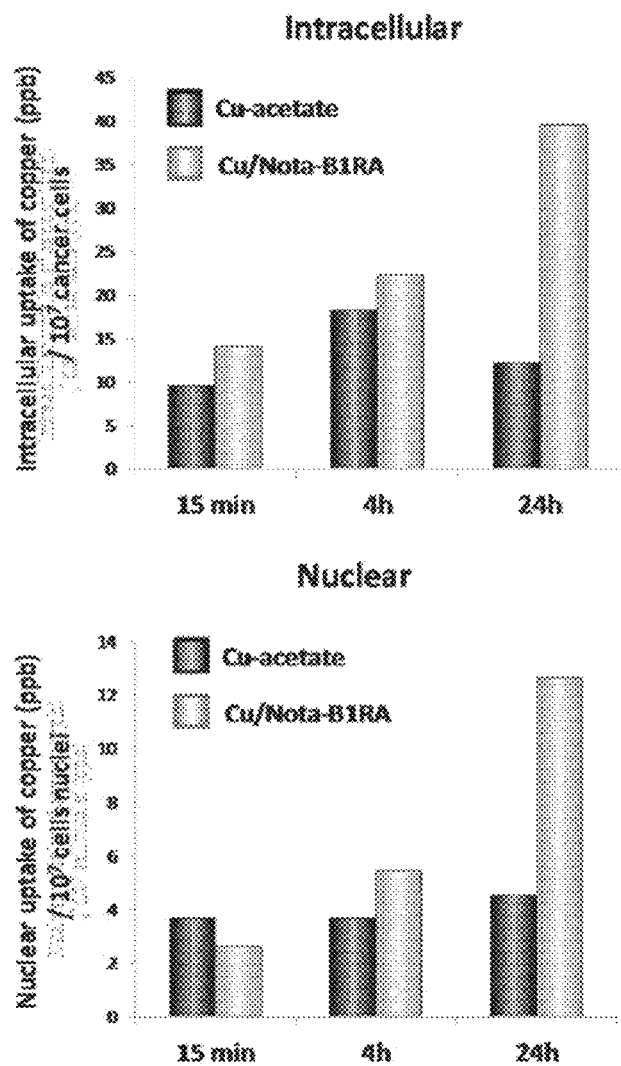
FIG. 3 illustrate in vitro uptake of free (non-radioactive) Cu-acetate and Cu-NOTA-βAla-Orn$^1$-Arg$^2$-Oic$^3$-Pro$^4$-Gly$^5$-(αMe)Phe$^6$-Ser$^7$-DβNal$^8$-Ile$^9$-OH (Cu/Nota-B1RA; SEQ ID NO: 6) by breast cancer cells determined by ICP-MS.
Figure 4:
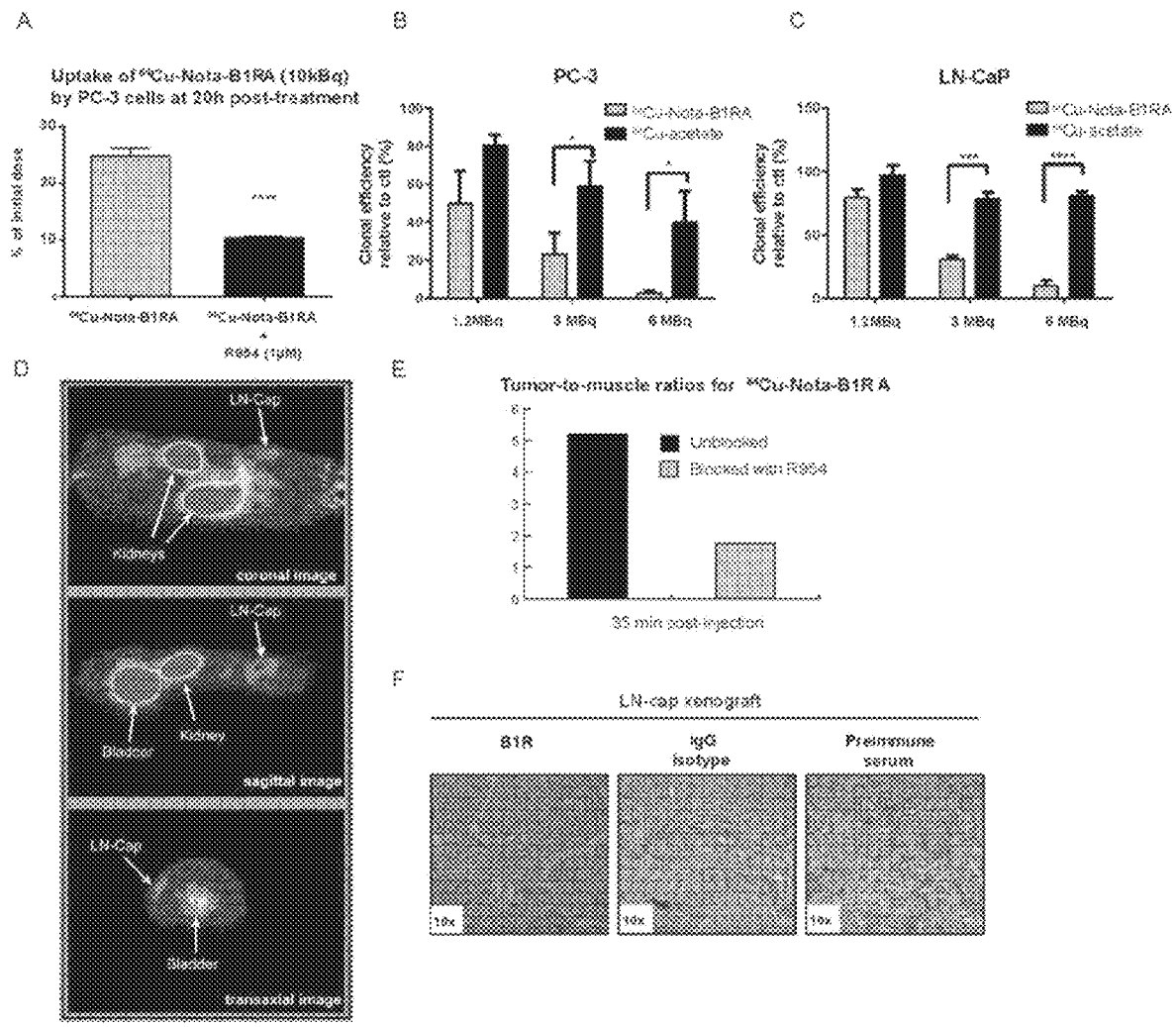
FIG. 4 illustrates in vitro efficacy of radiotherapy with $^{64}$Cu-NOTA-βAla-Orn$^1$-Arg$^2$-Oic$^3$-Pro$^4$-Gly$^5$-(αMe)Phe$^6$-Ser$^7$-DβNal$^8$-Ile$^9$-OH (SEQ ID NO: 6) assessed by clonogenic assays.
Figure 5:
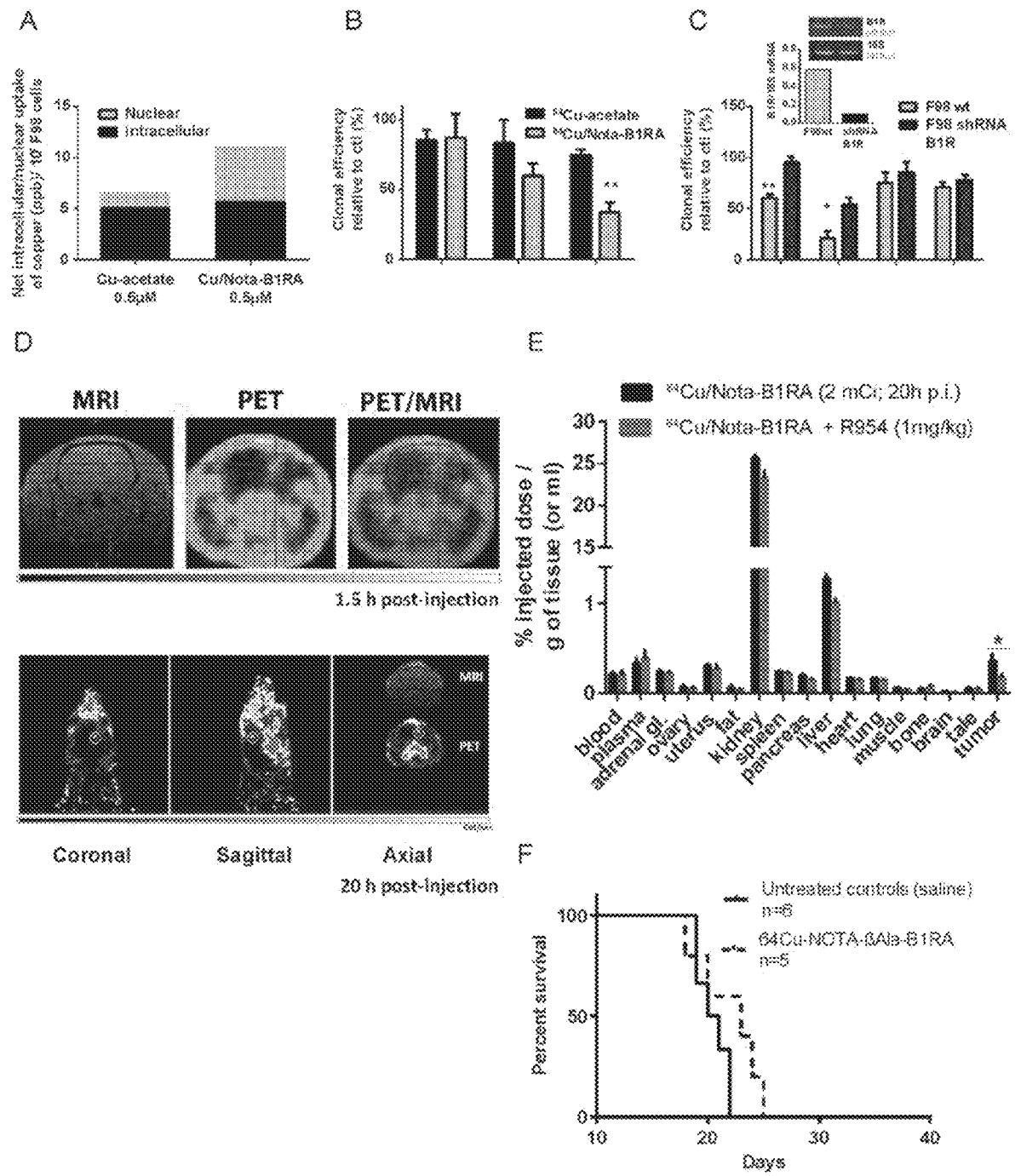
FIGS. 5A-C illustrate in vitro cellular/nuclear uptake and anticancer activity of $^{64}$Cu-NOTA-βAla-Orn$^1$-Arg$^2$-Oic$^3$-Pro$^4$-Gly$^5$-(αMe)Phe$^6$-Ser$^7$-DβNal$^8$-Ile$^9$-OH (Cu/Nota-B1RA) (SEQ ID NO: 6) in F98 GBM cells. Cell uptake and nuclear localization of non-radioactive, free Cu and Cu/Nota-B1RA in F98 glioma cells measured at 20 h post-treatment by ICP-MS (A). Dose-dependent antiproliferative effects of $^{64}$Cu-acetate, $^{64}$Cu/Nota-B1RA on F98 wildtype (B) or shRNA-B1R knockdown F98 cells (C) using clonogenic assays. Insert: Validation of B1R knockdown by RT-qPCR.
FIG. 5D illustrates brain imaging of Male Fisher rats bearing intracerebral rat F98 GBM cells 10 days after inoculation. MRI contrast-enhanced (Gd-DTPA) and PET brain imaging of 74 MBq (2 mCi) of intravenous $^{64}$Cu/Nota-B1RA at 1.5 h and at 20 h post-injection. Fusion of PET/MRI images of the same animal was obtained using PMOD software. PET signal intensity distribution is depicted in a pseudo-color map ranging from black (low) to white (high value).
FIG. 5E depicts the ex vivo biodistribution of $^{64}$Cu/Nota-B1RA in F98 GBM-bearing rats at 20 h post-injection.
FIG. 5F shows the Kaplan-Meier survival curves of F98 GBM-bearing rats following a single treatment with intravenous $^{64}$Cu/Nota-B1RA (7.5 mCi/rat), at day 10 post-inoculation.

It is disclosed herein an example of an encompassed theranostic consisting of the high-affinity, $^{64}$Cu-NOTA-βAla-Orn$^1$-Arg$^2$-Oic$^3$-Pro$^4$-Gly$^5$-(αMe)Phe$^6$-Ser$^7$-DβNal$^8$-Ile$^9$-OH (SEQ ID NO: 6) (FIG. 1B) that show 1) remarkable high in vitro/in vivo stability (revealing no degradation sign) in rats (FIG. 2), 2) favorable pharmacokinetics as it is largely eliminated by the kidneys in urine as intact form (FIG. 5), 3) important and unexpected ability to localize both in cytoplasmic and nuclear compartment of brain tumor cells and other types of cancer cells (e.g., breast and prostate), providing enhanced anticancer activity (FIGS. 3-5); such notable therapeutic efficacy of $^{64}$Cu/Nota-B1RA was not seen with $^{64}$Cu-acetate and the non-radioactive Cu/Nota- B1RA surrogate (up to 10 μM), 4) capacity to identify or detect non-invasively and rapidly human solid tumors (e.g., brain and prostate) expressing naturally-occurring native B1R (FIGS. 4 and 5), and 5) a tendency of prolonging survival using peptide receptor radionuclide therapy (PRRT) (FIG. 5).

Figure 6:
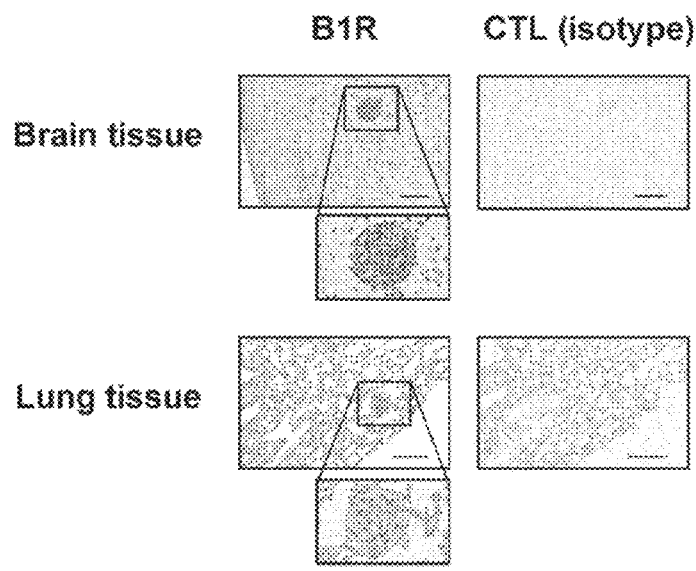
FIG. 6A illustrates the first report demonstrating B1R expression immunohistochemically (IHC) in mouse brain and lung metastases using a specific anti-B1R antiserum (blackest dark-color). FIG. B shows the bioluminescence and PET imaging of metastases (Mets) using the $^{64}$Cu-NOTA-βAla-Orn$^1$-Arg$^2$-Oic$^3$-Pro$^4$-Gly$^5$-(αMe)Phe$^6$-Ser$^7$-DβNal$^8$-Ile$^9$-OH (SEQ ID NO: 6) (7.4 MBq (0.2 mCi)) in the mouse 4T1/luc breast tumor model; white arrows indicate colocalization of PET imaging and bioluminescent signals in developed metastatic tumors in mice obtained 14 days after intracardiac inoculation of 4T1/luc cells.
Figure 6:
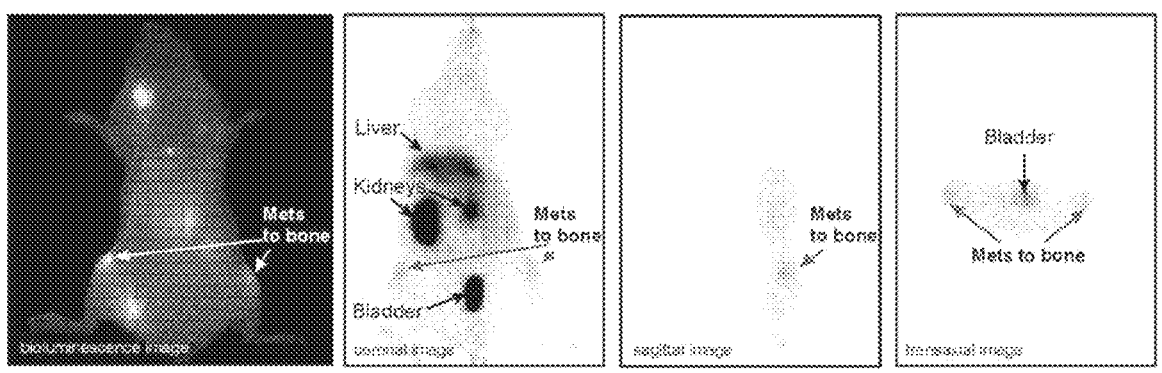

Small animal PET imaging was performed using the well-characterized and standardized syngeneic rat model of malignant brain glioblastoma (GBM), the rat Fischer/F98 malignant glioma model (FIG. 6), which is known to express B1R in both tumor vasculature and tumor cells. This orthotopic GBM model is particularly attractive for testing new therapeutic and diagnostic modalities as it simulates the behavior of human gliomas in terms of their highly invasive pattern of growth, low immunogenicity, resistance to a number of therapeutic modalities, and uniform lethality. The new results demonstrated that both intravenous $^{64}$Cu-labeled NOTA/B1R antagonist and agonist, namely $^{64}$Cu-NOTA-βAla-Orn$^1$-Arg$^2$-Oic$^3$-Pro$^4$-Gly$^5$-(αMe)Phe$^6$-Ser$^7$-DβNal$^8$-Ile$^9$-OH (SEQ ID NO: 6) (FIGS. 6A and B) and $^{64}$Cu-NOTA-βAla-DLys$^1$-Arg$^2$-Pro$^3$-Pro$^4$-Gly$^5$-Phe$^6$-Ser$^7$-Pro$^8$-DPhe$^9$-OH (SEQ ID NO: 38), properly detected relatively small brain tumors by μPET. $^{64}$Cu-NOTA-βAla-Orn$^1$-Arg$^2$-Oic$^3$-Pro$^4$-Gly$^5$-(αMe)Phe$^6$-Ser$^7$-DβNal$^8$-Ile$^9$-OH (SEQ ID NO: 6) showed very high and favorable brain tumor/contralateral background and brain tumor/muscle ratios at 20 h p.i. (ratios of 18:1 and 6:1, respectively). Control experiments using sham-operated animals, inoculated with F98-free DMEM, revealed the absence of PET signal in the brain after 10 days post-inoculation. Ex vivo biodistribution studies confirmed the PET imaging data with significant amount of brain tumor uptake of $^{64}$Cu-NOTA-βAla-Orn$^1$-Arg$^2$-Oic$^3$-Pro$^4$-Gly$^5$-(αMe)Phe$^6$-Ser$^7$-DβNal$^8$-Ile$^9$-OH (SEQ ID NO: 6). The B1R-targeted tumor uptake specificity of the new conjugate was confirmed by control experiments using competitive blockade with unlabeled excess R954 (1 mg/kg) and use of genetic F98 GBM/B1R knockdown stable clones.

The syngeneic 4T1/luc mouse mammary tumor brain metastasis model was used as an additional piece of evidence for the effectiveness of the compounds disclosed herein. This highly-metastatic tumor model recapitulates several features of advanced human breast cancer, including the ability to generate spontaneous lethal brain, lung and bone nodes metastases, and may be advocated as the model most closely representing the clinical situation in human cancer. This preclinical animal model of secondary cancers have been shown to endogenously express inducible B1R proteins (FIG. 6A). Whole animal bioluminescent imaging (right after injection of luciferin), performed to track luciferase-expressing breast cancer cells, validated the presence of metastases on day 15 p.i. (FIG. 6B). PET signals obtained with $^{64}$Cu-NOTA-βAla-Orn$^1$-Arg$^2$-Oic$^3$-Pro$^4$-Gly$^5$-(αMe)Phe$^6$-Ser$^7$-DβNal$^8$-Ile$^9$-OH (SEQ ID NO: 6) colocalized with bioluminescent signals from (bone) metastases (FIG. 6B).

Altogether, the proof-of-concept data provide the first indication of the efficacy of imaging primary and secondary (metastatic) brain cancers with novel B1R-targeted theranostics.

In an embodiment, the cancer patient would first receive a diagnostic dose of a peptide labeled with a radionuclide compatible with imaging procedures (e.g., PET). If adequate B1R localization at the site of disease is achieved, the patient could receive a therapeutic dose of the same peptide labeled with a radionuclide (e.g., $^{64}$Cu) capable of inducing curative effects as described herein.

The novel approach here described would provide a fast and highly-specific diagnostic, together with a therapy for treating the brain cancer, in an efficient, non-invasive manner.

The present disclosure will be more readily understood by referring to the following examples which are given to illustrate embodiments rather than to limit its scope.

Example I

Peptide Synthesis and Radiolabeling

The peptide synthesis was performed as an example on an automated system using Tentagel S RAM resin. The resin was first loaded in the reaction column of the automatic peptide synthesizer (Pioneer Peptide Synthesis system, Applied Biosystems, Foster City, Calif.), and Fmoc amino acids were added in a 3-fold excess using HATU in the presence of DI PEA. A deprotection step was performed using 20% piperidine in DMF. The NOTA chelate unit was synthetized as an example using the procedure described by Guerin et al. (2010, Org Lett, 12: 280-283). The N-terminal Fmoc was cleaved from the peptidyl resin using 20% piperidine for 30 min, followed by successive washing with DMF 2×, DCM 3×, IPA, DCM, IPA, DCM, IPA and DCM 3×. The resin was then treated with bromoacetic anhydride 2.5 fold equivalent (preformed in DCM with DIC (2.5 eq) and bromoacetic acid (5 eq), 15 min) for 30 min and then was wash as before. The resin was then suspended in DCM and 5-fold excess of 1,4,7-triazocyclononane was added followed by shaking for 3 h prior to wash and suspension in NMP. t-Butyl bromoacetate (3 eq) was added and shaken for 2 h before washing. The peptide was cleaved from the polymer solid support using a mixture of TFA/H$_2$O/TIPS (95/2.5/2.5, v/v/v) and stirred for 3 h. The mixture was filtered and the filtrate was precipitated in diethyl ether. The crude peptide was dissolved in a mixture of water and acetonitrile, filtered, dissolved in water, lyophilised and then purified with a preparative HPLC. The identity of the peptide was confirmed by mass spectrometry.

Peptides were labeled with $^{64}$Cu following conditions described in Guerin et al. (2010, Org Lett, 12: 280-283). Briefly, the peptides (3-5 nmol) were dissolved in ammonium acetate buffer (1 M, pH 7.4) with [$^{64}$Cu]Cu—(OAc)$_2$ (180-300 MBq; 5-8 mCi) in a total volume of 300-450 μL. The resulting solution was incubated at room temperature for 20-35 min. The labeled product was purified on a C-18 sep-Pack cartridge or by HPLC using a C-18 column and a radio-detector. The amount of radiolabeled peptide was determined by the peak area of the tracer in the UV-chromatogram compared to the UV peak area of the standard unlabeled peptide. The peptide fraction was collected, evaporated and counted in a Capintec radioisotope calibrator (Capintec, Inc., NJ, USA) to calculate the specific activity of the product.

Example II

In Vitro and In Vivo Assays

The apparent affinity constants (or potency) of kinin agonist and antagonist analogues for human B1R were estimated by in vitro human bioassay using isolated human umbilical veins (Gobeil et al., 1996, supra; Côté et al., 2009, supra). This tissue proved to be a valuable, natural and highly sensitive bioassay for determination of potency and selectivity of natural and synthetic kinin receptor ligands. It particularly expresses both kinin B1R and B2R at physiological densities. Apparent affinities of peptides were defined in terms of $EC_{50}$ ($pD_2$) values for agonists and $IC_{50}$ values for antagonists.

In vitro plasma stability of peptides was performed according to a previously published procedures (Fournier et al., 2012, Bioconjug Chem, 23:1687-1693). Briefly, an aliquot (20 µL) of the purified radiolabeled B1R peptides was mixed with 900 µL normal rat, mouse and human plasma. The mixture was incubated at 37° C. water bath for different periods of time in a shaking water bath, and then processed for UPLC analysis.

For in vivo stability studies in normal healthy rats and mice, peptide was reconstituted in PBS and 20-30 MBq (500-800 µCi; 100 µL) were injected through the tail vein to isoflurane anesthetized animals. At different times post-injection, blood and urine were collected, centrifuged and followed by a protein precipitation with acetonitrile. Samples were analyzed by UPLC using a C-18 column and a radio-detector. Analysis and retention times were compared to the original radiolabeled peptide to monitor peptide cleavage.

Cellular uptake profiles of non-radioactive Cu-acetate and Cu-labeled peptides in B1R expressing rat F98 GBM cells were evaluated by ICP-MS analysis. Brain cancer cells were allowed to grow to confluence on a 10-cm dish. Cells were then incubated with Cu-acetate or Cu-labeled peptides (500 nM) in FBS free-DMEM at 37° C. for 15 min or 1, 4, or 20 h, respectively. For determination of nonspecific internalization, one set of dishes was incubated with the potent B1R antagonist R-954 (1 µM) at 37° C. for 10 min to block B1R prior to incubation with Cu-labeled peptides. At each time point, media was collected, and cells were acid-washed once (50 mM acetic acid/250 mM NaCl pH 2.5), to remove surface-bound fractions, and then washed twice with Phosphate-buffered saline (PBS, pH 7.4). Thereafter, cells were trypsinized, collected by centrifugation and gently washed with Hank's buffered salt solution (HBSS). Cells were solubilized in 1/1 nitric acid/30% $H_2O_2$ solution, and the amount of Cu was determined by ICP-MS. Non-expressing B1R human embryonic kidney cells HEK-293T and/or stable B1R knock-down F98 GBM cells were used as controls to validate specificity of cellular ligand uptake. Alternatively, radiometric assays were used for the measurement of cellular incorporation of selected radioactive compounds as described by Couture et al. (2014, Neoplasia, 16(8): 634-643).

Irradiating DNA is an effective way to injure and eventually kill cells. A radionuclide that localizes to the cell nucleus of a tumor cell, thus potentially enhances the efficacy of the radiopharmaceutical. This may be especially true for radionuclides whose penetration ranges in tissues are relatively short such as $^{64}Cu$. Therefore, to realize the full therapeutical potential of Auger electron emitting isotopes, radionuclides must target not only the cytoplasm but also the nuclei of cancer cells. Thus, testing was done to determine whether or not nonradioactive Cu-acetate and Cu-labeled B1R compounds localize to the nucleus of cancer cells using the same ICP-MS technique as described above. Cell nuclei were isolated by cell fractionation techniques as described by Wang et al. (2003, Cancer Res, 63(20): 6864-6869) with slight modifications. Following treatments, cancer cells were trypsinized, centrifuged, and washed with HBSS, then resuspended in 1 ml of hypotonic buffer (10 mM PIPES pH 6,8, 100 mM NaCl, 2 mM $MgCl_2$, 300 mM Sucrose) containing 0.5% Triton X100 for 2 min on ice. Cell lysates were then diluted in 10 ml of detergent-free hypotonic buffer and centrifuged. Pelleted cell-free nuclei were resuspended in 0.5 ml of hypotonic buffer, counted and finally solubilized in 1/1 nitric acid/30% $H_2O_2$ solution. Purity of nuclei (>80%) was verified by light microscopy after trypan blue staining. Quantification of Cu content in the nuclear fractions was done by ICP-MS.

Cytotoxicity of B1R radionuclide therapy was assessed in cancer cells by clonogenic assays. Cells (600 cells/plate) were seeded into a 6-well cell culture plate, treated 48 h later with or without $^{64}Cu$-acetate or $^{64}Cu$-labeled B1R peptides (1, 10, 25, 50 and 100 nM), and incubated at 37° C. in serum-containing media for about 7-9 days. Then, media were removed and colonies fixed/stained with 0.5% methylene blue in 50% ethanol, rinsed with tap water and air dried. Colony counting was performed manually or automatically using the Image Pro Plus 5.1. Controls included treatments of cells with non-radioactive agents labeled similarly and use of stable shRNA knock-down F98 GBM cells (about 85-90% of mRNA depletion of B1R as assessed by RT-PCR).

The F98 GBM cell line (#CRL-2397) was purchased from American Type Culture Collection (ATCC). Cells were cultured as monolayers in Dulbecco's modified Eagle medium (DMEM) supplemented with 10% fetal bovine serum (FBS) and 1% penicillin-streptomycin mixture at 37° C. in a humidified 5% $CO_2$/95% air incubator. The procedure of F98 glioma cell implantation was similar to that used in our previous studies (Côté et al., 2010, Neuropeptides, 44:177-185). Briefly, F98 glioma cells ($1 \times 10^4$ cells in 5 µl) were injected into the region of the right caudate nucleus of the animals under ketamine: xylazine anesthesia (87 mg/kg: 13 mg/kg, i.p.) at the following stereotaxic coordinates: 1 mm anterior and 3 mm lateral to bregma, and 6 mm below the external table of the skull. Unless otherwise specified, tumors were allowed to grow for 10 days to mid-stage (approximately 15-20 $mm^3$) before the beginning of the in vivo (biodistribution and PET) experiments. All tumor transplantations were successful as determined by histology and/or MRI.

Ex vivo biodistribution studies were performed by injecting 74 MBq (2 mCi/rat; 100 µL) of $^{64}Cu$-NOTA-βAla-Orn$^1$-Arg$^2$-Oic$^3$-Pro$^4$-Gly$^5$-(αMe)Phe$^6$-Ser$^7$-DβNal$^8$-Ile$^9$-OH (SEQ ID NO: 6) to isoflurane-anesthetized normal (non-implanted) or F98 bearing rats via the caudal vein. After 1 and 20 h post-injection, the animals were euthanized by $CO_2$ inhalation. Organs of interest were further collected, weighed, and measured in a gamma-counter (Cobra II auto-gamma counter, Packard, Minn.). The results were expressed as percentage of the injected dose per gram of tissue (% ID/g). Specificity of brain tumor uptake of B1R radiotracers was determined by pre-administration of 1 mg/kg of R954 peptide (5 min prior the injection of the radiolabelled peptide) and using sham-operated contralaterals. Animals bearing B1R target knockdowns were also employed to further support specificity of brain tumor uptake. Experiments were realized with a minimum of 3 rats per group.

Example III

In Vivo Imaging

PET scans were performed using a LabPET8 (Gamma Medica Inc.) small animal scanner with an axial field of view of 8 cm. F98 GBM bearing rats were injected with 74 MBq (2 mCi; 100 µL) of novel $^{64}Cu$ radiolabeled B1R peptides (agonist or antagonist) with via the caudal vein under isoflurane anesthesia. PET scans were assessed 1 h and 20 h post-injections. Each animal had a 20 minutes scan after compound injection. The images were reconstructed by a three dimensional MLEM algorithm implementing an analytically derived system matrix (Selivanov et al., 2000, Nuclear Science, IEEE Transactions on, 47: 1168-1175). Regions of interest were traced for tumor, normal brain, heart, liver, kidney, and muscle, and the activity in each organ was measured and reported to the injected dose for percentages calculation. The specificity of each radiotracer for its target was demonstrated following pre-administration of excess unlabeled analogue as well as with stable B1R knock-downs of F98 GBM cells (vide supra). In vivo testing of the novel kinin PET radiotracers was also assessed in a model of tumor metastasis induced by the intracardiac injection of 4T1/luc (bioluminescent) mouse breast cancer cells under ultrasound guidance.

Example IV

Peptide Receptor Radionuclide Therapy (PRRT)

Single-Dose Radiotherapy Experiments: Rats bearing F98 GBM (pre-visualized by MRI) are injected (via the tail vein) within 10-12 day after implantation with a single intravenous dose of 100 µl of sterile PBS containing the $^{64}$Cu-BIR radiolabeled peptide antagonist and agonist; control group animals will receive the vehicle and equivalent moles of the unlabeled peptide antagonist and agonist. Contrast-enhanced $T_1$-weighted MR imaging and anatomic $T_2$-weighted on a 7-Tesla small animal system are performed in 3 rats randomly picked for each group, at days 6, 10, 20, 30 and 40 post-implantation to monitor tumor growth in vivo and treatment efficacy.

Multiple-Dose Radiotherapy Experiments: PRRT are given to rats bearing F98 GBM on day 3 and repeated on day 15 post-implantation. Control group animals are exactly the same as described in the single-dose therapy experiments. MRI data are used to monitor therapeutic response of $^{64}$Cu-BIR radiolabeled peptides and of the corresponding unlabeled peptides, as above-mentioned.

Survival times of brain cancer-bearing animals left untreated (controls receiving the vehicle only), treated with the unlabeled peptide antagonist and agonist and subjected to single- and multi-dose radiation therapy are estimated by Kaplan-Meier method and compared with log-rank test using the Graph Pad Prism 6.0 software.

While the invention has been described in connection with specific embodiments thereof, it will be understood that it is capable of further modifications and this application is intended to cover any variations, uses, or adaptations of the invention, including such departures from the present disclosure as come within known or customary practice within the art to which the invention pertains and as may be applied to the essential features hereinbefore set forth, and as follows in the scope of the appended claims.

What is claimed is:

1. A theranostic composition comprising a theranostic compound and a carrier, wherein the theranostic compound is:

$^{64}$Cu-NOTHA$_2$-βAla-Orn$^1$-Arg$^2$-Oic$^3$-Pro$^4$-Gly$^5$-(αMe)Phe$^6$-Ser$^7$-DβNal$^8$-Ile$^9$-OH;

$^{64}$Cu-NOTA-βAla-Orn$^1$-Arg$^2$-Oic$^3$-Pro$^4$-Gly$^5$-(αMe)Phe$^6$-Ser$^7$-DβNal$^8$-Ile$^9$-OH;

$^{64}$Cu-NOTA-Orn$^1$-Arg$^2$-Oic$^3$-Pro$^4$-Gly$^5$-(αMe)Phe$^6$-Ser$^7$-DβNal$^8$-Ile$^9$-OH;

$^{64}$Cu-NOTA-βAla-(L or D)Lys$^1$-Arg$^2$-Pro$^3$-Hyp$^4$-Gly$^5$-Igl$^6$-Ser$^7$-Pro$^8$-DPhe$^9$-OH;

$^{64}$Cu-NOTA-(L or D)Lys$^1$-Arg$^2$-Pro$^3$-Hyp$^4$-Gly$^5$-Igl$^6$-Ser$^7$-Pro$^8$-DPhe$^9$-OH;

$^{64}$Cu-NOTA-Lys$^1$-Arg$^2$-Oic$^3$-Pro$^4$-Gly$^5$-(αMe)Phe$^6$-Ser$^7$-DβNal$^8$-Ile$^9$-OH;

$^{64}$Cu-NOTA-βAla-Lys$^1$-Arg$^2$-Oic$^3$-Pro$^4$-Gly$^5$-(αMe)Phe$^6$-Ser$^7$-DβNal$^8$-Ile$^9$-OH;

$^{64}$Cu-NOTA-Arg$^1$-Arg$^2$-Oic$^3$-Pro$^4$-Gly$^5$-(αMe)Phe$^6$-Ser$^7$-DβNal$^8$-Ile$^9$-OH; or $^{64}$Cu-NOTA-βAla-Arg$^1$-Arg$^2$-Oic$^3$-Pro$^4$-Gly$^5$-(αMe)Phe$^6$-Ser$^7$-DβNal$^8$-Ile$^9$-OH.

2. The composition of claim 1, wherein said compound is in free base form or in salt form.

* * * * *

SEQUENCE LISTING

```
<160> NUMBER OF SEQ ID NOS: 43

<210> SEQ ID NO 1
<211> LENGTH: 9
<212> TYPE: PRT
<213> ORGANISM: Artificial Sequence
<220> FEATURE:
<223> OTHER INFORMATION: R954
<220> FEATURE:
<221> NAME/KEY: MOD_RES
<222> LOCATION: (1)...(1)
<223> OTHER INFORMATION: Orn
<220> FEATURE:
<221> NAME/KEY: SITE
<222> LOCATION: (3)...(3)
<223> OTHER INFORMATION: Xaa = 2-Carboxyoctahydroindole or Oic
<220> FEATURE:
<221> NAME/KEY: SITE
<222> LOCATION: (6)...(6)
<223> OTHER INFORMATION: alpha-methyl phenylalanine
<220> FEATURE:
<221> NAME/KEY: SITE
<222> LOCATION: (8)...(8)
<223> OTHER INFORMATION: Xaa = D-beta-(2-naphthyl)-alanine

<400> SEQUENCE: 1

Xaa Arg Xaa Pro Gly Phe Ser Xaa Ile
1               5

<210> SEQ ID NO 2
<211> LENGTH: 10
<212> TYPE: PRT
<213> ORGANISM: Artificial Sequence
<220> FEATURE:
<221> NAME/KEY: MOD_RES
<222> LOCATION: (1)...(1)
<223> OTHER INFORMATION: MeGly
<220> FEATURE:
<221> NAME/KEY: SITE
<222> LOCATION: (5)...(5)
```

```
<223> OTHER INFORMATION: Xaa = hydroxyproline
<220> FEATURE:
<221> NAME/KEY: SITE
<222> LOCATION: (10)...(10)
<223> OTHER INFORMATION: D-phenylalanine
<220> FEATURE:
<223> OTHER INFORMATION: Chemically synthesized

<400> SEQUENCE: 2

Xaa Lys Arg Pro Xaa Gly Phe Ser Pro Phe
1               5                   10

<210> SEQ ID NO 3
<211> LENGTH: 9
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: D-lysine
<220> FEATURE:
<221> NAME/KEY: SITE
<222> LOCATION: (4)...(4)
<223> OTHER INFORMATION: Xaa = hydroxyproline
<220> FEATURE:
<221> NAME/KEY: SITE
<222> LOCATION: (6)...(6)
<223> OTHER INFORMATION: Xaa = 2-indanylglycine
<220> FEATURE:
<221> NAME/KEY: SITE
<222> LOCATION: (9)...(9)
<223> OTHER INFORMATION: D-phenylalanine

<400> SEQUENCE: 3

Lys Arg Pro Xaa Gly Xaa Ser Pro Phe
1               5

<210> SEQ ID NO 4
<211> LENGTH: 9
<212> TYPE: PRT
<213> ORGANISM: Artificial Sequence
<220> FEATURE:
<223> OTHER INFORMATION: Chemically synthesized
<220> FEATURE:
<221> NAME/KEY: MOD_RES
<222> LOCATION: (1)...(1)
<223> OTHER INFORMATION: Orn
<220> FEATURE:
<221> NAME/KEY: SITE
<222> LOCATION: (4)...(4)
<223> OTHER INFORMATION: Xaa = hydroxyproline
<220> FEATURE:
<221> NAME/KEY: SITE
<222> LOCATION: (6)...(6)
<223> OTHER INFORMATION: Xaa = 2-indanylglycine
<220> FEATURE:
<221> NAME/KEY: SITE
<222> LOCATION: (9)...(9)
<223> OTHER INFORMATION: D-phenylalanine

<400> SEQUENCE: 4

Xaa Arg Pro Xaa Gly Xaa Ser Pro Phe
1               5

<210> SEQ ID NO 5
<211> LENGTH: 9
<212> TYPE: PRT
<213> ORGANISM: Artificial Sequence
<220> FEATURE:
<223> OTHER INFORMATION: Chemically synthesized
<220> FEATURE:
```

```
<221> NAME/KEY: MOD_RES
<222> LOCATION: (1)...(1)
<223> OTHER INFORMATION: Orn
<220> FEATURE:
<221> NAME/KEY: SITE
<222> LOCATION: (3)...(3)
<223> OTHER INFORMATION: Xaa = 2-Carboxyoctahydroindole
<220> FEATURE:
<221> NAME/KEY: SITE
<222> LOCATION: (6)...(6)
<223> OTHER INFORMATION: alpha-methyl-phenylalanine
<220> FEATURE:
<221> NAME/KEY: SITE
<222> LOCATION: (8)...(8)
<223> OTHER INFORMATION: Xaa = D-beta-(2-naphthyl)-alanine

<400> SEQUENCE: 5

Xaa Arg Xaa Pro Gly Phe Ser Xaa Ile
1               5

<210> SEQ ID NO 6
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: MOD_RES
<222> LOCATION: (2)...(2)
<223> OTHER INFORMATION: Orn
<220> FEATURE:
<221> NAME/KEY: SITE
<222> LOCATION: (4)...(4)
<223> OTHER INFORMATION: Xaa = 2-Carboxyoctahydroindole
<220> FEATURE:
<221> NAME/KEY: SITE
<222> LOCATION: (7)...(7)
<223> OTHER INFORMATION: alpha-methyl-phenylalanine
<220> FEATURE:
<221> NAME/KEY: SITE
<222> LOCATION: (9)...(9)
<223> OTHER INFORMATION: Xaa = D-beta-(2-naphthyl)-alanine

<400> SEQUENCE: 6

Ala Xaa Arg Xaa Pro Gly Phe Ser Xaa Ile
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: SITE
<222> LOCATION: (2)...(2)
<223> OTHER INFORMATION: D-lysine
<220> FEATURE:
<221> NAME/KEY: SITE
<222> LOCATION: (5)...(5)
<223> OTHER INFORMATION: Xaa = hydroxypolin
<220> FEATURE:
<221> NAME/KEY: SITE
<222> LOCATION: (7)...(7)
<223> OTHER INFORMATION: Xaa = 2-indanylglycine
<220> FEATURE:
<221> NAME/KEY: SITE
```

```
<222> LOCATION: (10)...(10)
<223> OTHER INFORMATION: D-phenylalanine

<400> SEQUENCE: 7

Ala Lys Arg Pro Xaa Gly Xaa Ser Pro Phe
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: MOD_RES
<222> LOCATION: (2)...(2)
<223> OTHER INFORMATION: Orn
<220> FEATURE:
<221> NAME/KEY: SITE
<222> LOCATION: (5)...(5)
<223> OTHER INFORMATION: Xaa = hydroxyprolin
<220> FEATURE:
<221> NAME/KEY: SITE
<222> LOCATION: (7)...(7)
<223> OTHER INFORMATION: Xaa = 2-indanylglycine
<220> FEATURE:
<221> NAME/KEY: SITE
<222> LOCATION: (10)...(10)
<223> OTHER INFORMATION: D-phenylalanine

<400> SEQUENCE: 8

Ala Xaa Arg Pro Xaa Gly Xaa Ser Pro Phe
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: MOD_RES
<222> LOCATION: (2)...(2)
<223> OTHER INFORMATION: Orn
<220> FEATURE:
<221> NAME/KEY: SITE
<222> LOCATION: (4)...(4)
<223> OTHER INFORMATION: Xaa = 2-Carboxyoctahydroindole
<220> FEATURE:
<221> NAME/KEY: SITE
<222> LOCATION: (7)...(7)
<223> OTHER INFORMATION: Xaa = cyclohexyl-alanine
<220> FEATURE:
<221> NAME/KEY: SITE
<222> LOCATION: (9)...(9)
<223> OTHER INFORMATION: Xaa = D-beta-(2-naphthyl)-alanine

<400> SEQUENCE: 9

Ala Xaa Arg Xaa Pro Gly Xaa Ser Xaa Ile
1               5                   10

<210> SEQ ID NO 10
<211> LENGTH: 10
<212> TYPE: PRT
<213> ORGANISM: Artificial Sequence
```

```
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: MOD_RES
<222> LOCATION: (2)...(2)
<223> OTHER INFORMATION: Orn
<220> FEATURE:
<221> NAME/KEY: SITE
<222> LOCATION: (4)...(4)
<223> OTHER INFORMATION: Xaa = 2-Carboxyoctahydroindole
<220> FEATURE:
<221> NAME/KEY: SITE
<222> LOCATION: (7)...(7)
<223> OTHER INFORMATION: Xaa = 2-indanylglycine
<220> FEATURE:
<221> NAME/KEY: SITE
<222> LOCATION: (9)...(9)
<223> OTHER INFORMATION: D-beta-(2-naphthyl)-alanine

<400> SEQUENCE: 10

Ala Xaa Arg Xaa Pro Gly Xaa Ser Xaa Ile
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: MOD_RES
<222> LOCATION: (2)...(2)
<223> OTHER INFORMATION: Orn
<220> FEATURE:
<221> NAME/KEY: SITE
<222> LOCATION: (4)...(4)
<223> OTHER INFORMATION: Xaa = 2-Carboxyoctahydroindole
<220> FEATURE:
<221> NAME/KEY: SITE
<222> LOCATION: (7)...(7)
<223> OTHER INFORMATION: Xaa = alpha-(2-thienyl)-L-alanine
<220> FEATURE:
<221> NAME/KEY: SITE
<222> LOCATION: (9)...(9)
<223> OTHER INFORMATION: Xaa = D-beta-(2-naphthyl)-alanine

<400> SEQUENCE: 11

Ala Xaa Arg Xaa Pro Gly Xaa Ser Xaa Ile
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: MOD_RES
<222> LOCATION: (2)...(2)
<223> OTHER INFORMATION: Orn
<220> FEATURE:
<221> NAME/KEY: SITE
<222> LOCATION: (4)...(4)
```

```
<223> OTHER INFORMATION: Xaa = 2-Carboxyoctahydroindole
<220> FEATURE:
<221> NAME/KEY: SITE
<222> LOCATION: (7)...(7)
<223> OTHER INFORMATION: D or L-alpha-cyclopentyl-alanine
<220> FEATURE:
<221> NAME/KEY: SITE
<222> LOCATION: (9)...(9)
<223> OTHER INFORMATION: D-beta-(2-naphthyl)-alanine

<400> SEQUENCE: 12

Ala Xaa Arg Xaa Pro Gly Xaa Ser Xaa Ile
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: SITE
<222> LOCATION: (2)...(2)
<223> OTHER INFORMATION: L or D-lysine
<220> FEATURE:
<221> NAME/KEY: SITE
<222> LOCATION: (4)...(4)
<223> OTHER INFORMATION: Xaa = 2-Carboxyoctahydroindole
<220> FEATURE:
<221> NAME/KEY: SITE
<222> LOCATION: (7)...(7)
<223> OTHER INFORMATION: alpha-methyl-phenylalanine
<220> FEATURE:
<221> NAME/KEY: SITE
<222> LOCATION: (9)...(9)
<223> OTHER INFORMATION: Xaa = D-beta-(2-naphthyl)-alanine

<400> SEQUENCE: 13

Ala Lys Arg Xaa Pro Gly Phe Ser Xaa Ile
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: SITE
<222> LOCATION: (2)...(2)
<223> OTHER INFORMATION: L or D-lysine
<220> FEATURE:
<221> NAME/KEY: SITE
<222> LOCATION: (4)...(4)
<223> OTHER INFORMATION: Xaa = 2-Carboxyoctahydroindole
<220> FEATURE:
<221> NAME/KEY: SITE
<222> LOCATION: (7)...(7)
<223> OTHER INFORMATION: Xaa = cyclohexyl-alanine
<220> FEATURE:
<221> NAME/KEY: SITE
<222> LOCATION: (9)...(9)
<223> OTHER INFORMATION: Xaa = D-beta-(2-naphthyl)-alanine

<400> SEQUENCE: 14

Ala Lys Arg Xaa Pro Gly Xaa Ser Xaa Ile
```

```
1               5                   10
```

<210> SEQ ID NO 15
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: SITE
<222> LOCATION: (2)...(2)
<223> OTHER INFORMATION: L or D-lysine
<220> FEATURE:
<221> NAME/KEY: SITE
<222> LOCATION: (4)...(4)
<223> OTHER INFORMATION: Xaa = 2-Carboxyoctahydroindole
<220> FEATURE:
<221> NAME/KEY: SITE
<222> LOCATION: (7)...(7)
<223> OTHER INFORMATION: Xaa =2-indanylglycine
<220> FEATURE:
<221> NAME/KEY: SITE
<222> LOCATION: (9)...(9)
<223> OTHER INFORMATION: Xaa = D-beta-(2-napththyl)-alanine

<400> SEQUENCE: 15

```
Ala Lys Arg Xaa Pro Gly Xaa Ser Xaa Ile
1               5                   10
```

<210> SEQ ID NO 16
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: SITE
<222> LOCATION: (2)...(2)
<223> OTHER INFORMATION: L or D-lysine
<220> FEATURE:
<221> NAME/KEY: SITE
<222> LOCATION: (4)...(4)
<223> OTHER INFORMATION: Xaa = 2-Carboxyoctahydroindole
<220> FEATURE:
<221> NAME/KEY: SITE
<222> LOCATION: (7)...(7)
<223> OTHER INFORMATION: Xaa = alpha(2-thienyl)-L-alanine
<220> FEATURE:
<221> NAME/KEY: SITE
<222> LOCATION: (9)...(9)
<223> OTHER INFORMATION: Xaa = D-beta-(2-naphthyl)-alanine

<400> SEQUENCE: 16

```
Ala Lys Arg Xaa Pro Gly Xaa Ser Xaa Ile
1               5                   10
```

<210> SEQ ID NO 17
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine

```
<220> FEATURE:
<221> NAME/KEY: SITE
<222> LOCATION: (2)..(2)
<223> OTHER INFORMATION: L or D-lysine
<220> FEATURE:
<221> NAME/KEY: SITE
<222> LOCATION: (4)..(4)
<223> OTHER INFORMATION: Xaa = 2-Carboxyoctahydroindole
<220> FEATURE:
<221> NAME/KEY: SITE
<222> LOCATION: (7)..(7)
<223> OTHER INFORMATION: Xaa = L or D-alpha-cyclopentyl-alanine
<220> FEATURE:
<221> NAME/KEY: SITE
<222> LOCATION: (9)..(9)
<223> OTHER INFORMATION: Xaa = D-beta-(2-naphthyl)-alanine

<400> SEQUENCE: 17

Ala Lys Arg Xaa Pro Gly Xaa Ser Xaa Ile
 1               5                  10

<210> SEQ ID NO 18
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)..(1)
<223> OTHER INFORMATION: beta-alanine
<220> FEATURE:
<221> NAME/KEY: SITE
<222> LOCATION: (2)..(2)
<223> OTHER INFORMATION: L or D-arginine
<220> FEATURE:
<221> NAME/KEY: SITE
<222> LOCATION: (4)..(4)
<223> OTHER INFORMATION: Xaa = 2-Carboxyoctahydroindole
<220> FEATURE:
<221> NAME/KEY: SITE
<222> LOCATION: (7)..(7)
<223> OTHER INFORMATION: alpha-methyl-phenylalanine
<220> FEATURE:
<221> NAME/KEY: SITE
<222> LOCATION: (9)..(9)
<223> OTHER INFORMATION: Xaa = D-beta-(2-naphthyl)-alanine

<400> SEQUENCE: 18

Ala Arg Arg Xaa Pro Gly Phe Ser Xaa Ile
 1               5                  10

<210> SEQ ID NO 19
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)..(1)
<223> OTHER INFORMATION: beta-alanine
<220> FEATURE:
<221> NAME/KEY: SITE
<222> LOCATION: (2)..(2)
<223> OTHER INFORMATION: L or D-arginine
<220> FEATURE:
<221> NAME/KEY: SITE
<222> LOCATION: (4)..(4)
<223> OTHER INFORMATION: Xaa = 2-Carboxyoctahydroindole
<220> FEATURE:
<221> NAME/KEY: SITE
<222> LOCATION: (7)..(7)
<223> OTHER INFORMATION: Xaa = cyclohexyl-alanine
<220> FEATURE:
```

```
<221> NAME/KEY: SITE
<222> LOCATION: (9)...(9)
<223> OTHER INFORMATION: Xaa =D-beta-(2-naphthyl)-alanine

<400> SEQUENCE: 19

Ala Arg Arg Xaa Pro Gly Xaa Ser Xaa Ile
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: SITE
<222> LOCATION: (2)...(2)
<223> OTHER INFORMATION: L or D-arginine
<220> FEATURE:
<221> NAME/KEY: SITE
<222> LOCATION: (4)...(4)
<223> OTHER INFORMATION: Xaa = 2-Carboxyoctahydroindole
<220> FEATURE:
<221> NAME/KEY: SITE
<222> LOCATION: (7)...(7)
<223> OTHER INFORMATION: Xaa = 2-indanylglycine
<220> FEATURE:
<221> NAME/KEY: SITE
<222> LOCATION: (9)...(9)
<223> OTHER INFORMATION: Xaa = D-beta-(2-naphthyl)-alanine

<400> SEQUENCE: 20

Ala Arg Arg Xaa Pro Gly Xaa Ser Xaa Ile
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: SITE
<222> LOCATION: (2)...(2)
<223> OTHER INFORMATION: L or D-arginine
<220> FEATURE:
<221> NAME/KEY: SITE
<222> LOCATION: (4)...(4)
<223> OTHER INFORMATION: Xaa = 2-Carboxyoctahydroindole
<220> FEATURE:
<221> NAME/KEY: SITE
<222> LOCATION: (7)...(7)
<223> OTHER INFORMATION: Xaa = alpha-(2-thienyl)-L-alanine
<220> FEATURE:
<221> NAME/KEY: SITE
<222> LOCATION: (9)...(9)
<223> OTHER INFORMATION: Xaa = D-beta-(2-naphthyl)-alanine

<400> SEQUENCE: 21

Ala Arg Arg Xaa Pro Gly Xaa Ser Xaa Ile
1               5                   10

<210> SEQ ID NO 22
<211> LENGTH: 10
<212> TYPE: PRT
```

```
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: SITE
<222> LOCATION: (4)...(4)
<223> OTHER INFORMATION: Xaa = 2-Carboxyoctahydroindole
<220> FEATURE:
<221> NAME/KEY: SITE
<222> LOCATION: (7)...(7)
<223> OTHER INFORMATION: Xaa = L or D-alpha-cyclopentyl-alanine
<220> FEATURE:
<221> NAME/KEY: SITE
<222> LOCATION: (9)...(9)
<223> OTHER INFORMATION: Xaa = D-beta-(2-naphthyl)-alanine

<400> SEQUENCE: 22

Ala Arg Arg Xaa Pro Gly Xaa Ser Xaa Ile
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: MOD_RES
<222> LOCATION: (2)...(2)
<223> OTHER INFORMATION: Orn
<220> FEATURE:
<221> NAME/KEY: SITE
<222> LOCATION: (7)...(7)
<223> OTHER INFORMATION: Xaa = L or D-alpha-cyclopentyl-alanine
<220> FEATURE:
<221> NAME/KEY: SITE
<222> LOCATION: (10)...(10)
<223> OTHER INFORMATION: D-phenylalanine

<400> SEQUENCE: 23

Ala Xaa Arg Pro Pro Gly Xaa Ser Pro Phe
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: MOD_RES
<222> LOCATION: (2)...(2)
<223> OTHER INFORMATION: Orn
<220> FEATURE:
<221> NAME/KEY: SITE
<222> LOCATION: (7)...(7)
<223> OTHER INFORMATION: alpha-methyl-phenylalanine
<220> FEATURE:
<221> NAME/KEY: SITE
<222> LOCATION: (10)...(10)
<223> OTHER INFORMATION: D-phenylalanine

<400> SEQUENCE: 24
```

```
Ala Xaa Arg Pro Pro Gly Phe Ser Pro Phe
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: MOD_RES
<222> LOCATION: (2)...(2)
<223> OTHER INFORMATION: Orn
<220> FEATURE:
<221> NAME/KEY: SITE
<222> LOCATION: (7)...(7)
<223> OTHER INFORMATION: L or D-phenylalanine
<220> FEATURE:
<221> NAME/KEY: SITE
<222> LOCATION: (10)...(10)
<223> OTHER INFORMATION: D-phenylalanine

<400> SEQUENCE: 25

Ala Xaa Arg Pro Pro Gly Phe Ser Pro Phe
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: MOD_RES
<222> LOCATION: (2)...(2)
<223> OTHER INFORMATION: Orn
<220> FEATURE:
<221> NAME/KEY: SITE
<222> LOCATION: (7)...(7)
<223> OTHER INFORMATION: Xaa = L or D-cyclohexyl-alanine
<220> FEATURE:
<221> NAME/KEY: SITE
<222> LOCATION: (10)...(10)
<223> OTHER INFORMATION: D-phenylalanine

<400> SEQUENCE: 26

Ala Xaa Arg Pro Pro Gly Xaa Ser Pro Phe
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: MOD_RES
<222> LOCATION: (2)...(2)
<223> OTHER INFORMATION: Orn
<220> FEATURE:
<221> NAME/KEY: SITE
```

```
<222> LOCATION: (7)...(7)
<223> OTHER INFORMATION: Xaa = L or D-2-indanylglycine
<220> FEATURE:
<221> NAME/KEY: SITE
<222> LOCATION: (10)...(10)
<223> OTHER INFORMATION: D-phenylalanine

<400> SEQUENCE: 27

Ala Xaa Arg Pro Pro Gly Xaa Ser Pro Phe
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: SITE
<222> LOCATION: (2)...(2)
<223> OTHER INFORMATION: L or D-lysine
<220> FEATURE:
<221> NAME/KEY: SITE
<222> LOCATION: (7)...(7)
<223> OTHER INFORMATION: L or D-phenylalanine
<220> FEATURE:
<221> NAME/KEY: SITE
<222> LOCATION: (10)...(10)
<223> OTHER INFORMATION: D-phenylalanine

<400> SEQUENCE: 28

Ala Lys Arg Pro Pro Gly Phe Ser Pro Phe
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: SITE
<222> LOCATION: (2)...(2)
<223> OTHER INFORMATION: L or D-lysine
<220> FEATURE:
<221> NAME/KEY: SITE
<222> LOCATION: (7)...(7)
<223> OTHER INFORMATION: L or D-phenylalanine
<220> FEATURE:
<221> NAME/KEY: SITE
<222> LOCATION: (10)...(10)
<223> OTHER INFORMATION: D-phenylalanine

<400> SEQUENCE: 29

Ala Lys Arg Pro Pro Gly Phe Ser Pro Phe
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
```

```
<222> LOCATION: (1)...(1)
<223> OTHER INFORMATION: beta-alanine
<220> FEATURE:
<221> NAME/KEY: SITE
<222> LOCATION: (2)...(2)
<223> OTHER INFORMATION: L or D-lysine
<220> FEATURE:
<221> NAME/KEY: SITE
<222> LOCATION: (7)...(7)
<223> OTHER INFORMATION: Xaa = L or D-cyclohexyl-alanine
<220> FEATURE:
<221> NAME/KEY: SITE
<222> LOCATION: (10)...(10)
<223> OTHER INFORMATION: D-phenylalanine

<400> SEQUENCE: 30

Ala Lys Arg Pro Pro Gly Xaa Ser Pro Phe
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: SITE
<222> LOCATION: (2)...(2)
<223> OTHER INFORMATION: L or D-lysine
<220> FEATURE:
<221> NAME/KEY: SITE
<222> LOCATION: (7)...(7)
<223> OTHER INFORMATION: Xaa = L or D-2-indanylglycine
<220> FEATURE:
<221> NAME/KEY: SITE
<222> LOCATION: (10)...(10)
<223> OTHER INFORMATION: D-phenylalanine

<400> SEQUENCE: 31

Ala Lys Arg Pro Pro Gly Xaa Ser Pro Phe
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: SITE
<222> LOCATION: (2)...(2)
<223> OTHER INFORMATION: L or D-lysine
<220> FEATURE:
<221> NAME/KEY: SITE
<222> LOCATION: (7)...(7)
<223> OTHER INFORMATION: Xaa = L or D-alpha-cyclopentyl-alanine
<220> FEATURE:
<221> NAME/KEY: SITE
<222> LOCATION: (10)...(10)
<223> OTHER INFORMATION: D-phenylalanine

<400> SEQUENCE: 32

Ala Lys Arg Pro Pro Gly Xaa Ser Pro Phe
1               5                   10
```

```
<210> SEQ ID NO 33
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: SITE
<222> LOCATION: (2)...(2)
<223> OTHER INFORMATION: L or D-arginine
<220> FEATURE:
<221> NAME/KEY: SITE
<222> LOCATION: (7)...(7)
<223> OTHER INFORMATION: L or D phenylalanine
<220> FEATURE:
<221> NAME/KEY: SITE
<222> LOCATION: (10)...(10)
<223> OTHER INFORMATION: D-phenylalanine

<400> SEQUENCE: 33

Ala Arg Arg Pro Pro Gly Phe Ser Pro Phe
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: SITE
<222> LOCATION: (2)...(2)
<223> OTHER INFORMATION: L or D-arginine
<220> FEATURE:
<221> NAME/KEY: SITE
<222> LOCATION: (7)...(7)
<223> OTHER INFORMATION: Xaa = L or D-cyclohexyl-alanine
<220> FEATURE:
<221> NAME/KEY: SITE
<222> LOCATION: (10)...(10)
<223> OTHER INFORMATION: D-phenilalanine

<400> SEQUENCE: 34

Ala Arg Arg Pro Pro Gly Xaa Ser Pro Phe
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: SITE
<222> LOCATION: (2)...(2)
<223> OTHER INFORMATION: L or D-arginine
<220> FEATURE:
<221> NAME/KEY: SITE
<222> LOCATION: (7)...(7)
<223> OTHER INFORMATION: Xaa = L or D-2-indanylglycine
<220> FEATURE:
<221> NAME/KEY: SITE
<222> LOCATION: (10)...(10)
```

```
<223> OTHER INFORMATION: D-phenylalanine

<400> SEQUENCE: 35

Ala Arg Arg Pro Pro Gly Xaa Ser Pro Phe
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: SITE
<222> LOCATION: (2)...(2)
<223> OTHER INFORMATION: L or D-arginine
<220> FEATURE:
<221> NAME/KEY: SITE
<222> LOCATION: (7)...(7)
<223> OTHER INFORMATION: Xaa = L or D-alpha-cyclopentyl-alanine
<220> FEATURE:
<221> NAME/KEY: SITE
<222> LOCATION: (10)...(10)
<223> OTHER INFORMATION: D-phenylalanine

<400> SEQUENCE: 36

Ala Arg Arg Pro Pro Gly Xaa Ser Pro Phe
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: MOD_RES
<222> LOCATION: (2)...(2)
<223> OTHER INFORMATION: Orn
<220> FEATURE:
<221> NAME/KEY: SITE
<222> LOCATION: (7)...(7)
<223> OTHER INFORMATION: Xaa = L or D-alpha-cyclopentyl-alanine
<220> FEATURE:
<221> NAME/KEY: SITE
<222> LOCATION: (10)...(10)
<223> OTHER INFORMATION: D-phenylalanine

<400> SEQUENCE: 37

Ala Xaa Arg Pro Pro Gly Xaa Ser Pro Phe
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: SITE
<222> LOCATION: (2)...(2)
```

```
<223> OTHER INFORMATION: D-lysine
<220> FEATURE:
<221> NAME/KEY: SITE
<222> LOCATION: (10)...(10)
<223> OTHER INFORMATION: D-phenylalanine

<400> SEQUENCE: 38

Ala Lys Arg Pro Pro Gly Phe Ser Pro Phe
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: SITE
<222> LOCATION: (10)...(10)
<223> OTHER INFORMATION: D-phenylalanine

<400> SEQUENCE: 39

Ala Lys Arg Pro Pro Gly Phe Ser Pro Phe
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: SITE
<222> LOCATION: (10)...(10)
<223> OTHER INFORMATION: D-phenylalanine

<400> SEQUENCE: 40

Ala Arg Arg Pro Pro Gly Phe Ser Pro Phe
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: SITE
<222> LOCATION: (2)...(2)
<223> OTHER INFORMATION: N((epsilon)-methyl)-lysine
<220> FEATURE:
<221> NAME/KEY: SITE
<222> LOCATION: (10)...(10)
<223> OTHER INFORMATION: D-phenylalanine

<400> SEQUENCE: 41

Ala Lys Arg Pro Pro Gly Phe Ser Pro Phe
1               5                   10
```

```
<210> SEQ ID NO 42
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: SITE
<222> LOCATION: (2)...(2)
<223> OTHER INFORMATION: (N(alpha)-methyl)-lysine
<220> FEATURE:
<221> NAME/KEY: SITE
<222> LOCATION: (10)...(10)
<223> OTHER INFORMATION: D-phenylalanine

<400> SEQUENCE: 42

Ala Lys Arg Pro Pro Gly Phe Ser Pro Phe
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: SITE
<222> LOCATION: (1)...(1)
<223> OTHER INFORMATION: beta-alanine
<220> FEATURE:
<221> NAME/KEY: SITE
<222> LOCATION: (2)...(2)
<223> OTHER INFORMATION: lysine(psi)(CH2-NH)
<220> FEATURE:
<221> NAME/KEY: SITE
<222> LOCATION: (10)...(10)
<223> OTHER INFORMATION: D-phenylalanine

<400> SEQUENCE: 43

Ala Lys Arg Pro Pro Gly Phe Ser Pro Phe
1               5                   10
```